(12) United States Patent
Stachelscheid et al.

(10) Patent No.: US 9,284,531 B2
(45) Date of Patent: Mar. 15, 2016

(54) DIFFERENTIATION OF HUMAN PLURIPOTENT STEM CELLS INTO CELLS EXPRESSING MATURE HEPATOCYTE MARKERS BY 2D AND BIOREACTOR CULTURE

(75) Inventors: Harald Stachelscheid, Berlin (DE); Katrin Zeilinger, Berlin (DE); Janne Jensen, Gothenburg (SE); Thomas Urbaniak, Berlin (DE)

(73) Assignee: Takara Bio Europe AB, Goteborg (SE)

( * ) Notice: Subject to any disclaimer, the term of this patent is extended or adjusted under 35 U.S.C. 154(b) by 392 days.

(21) Appl. No.: 13/376,610

(22) PCT Filed: Jun. 18, 2010

(86) PCT No.: PCT/EP2010/058679
§ 371 (c)(1),
(2), (4) Date: Jan. 23, 2012

(87) PCT Pub. No.: WO2010/149597
PCT Pub. Date: Dec. 29, 2010

(65) Prior Publication Data
US 2012/0115226 A1 May 10, 2012

Related U.S. Application Data

(60) Provisional application No. 61/218,140, filed on Jun. 18, 2009.

(30) Foreign Application Priority Data

Jun. 18, 2009 (DK) ................................ 2009 00751

(51) Int. Cl.
*C12N 15/85* (2006.01)
*C12N 5/071* (2010.01)
*C12M 1/12* (2006.01)

(52) U.S. Cl.
CPC ............... *C12N 5/067* (2013.01); *C12M 25/10* (2013.01); *C12N 5/0671* (2013.01); *C12N 2500/25* (2013.01); *C12N 2500/34* (2013.01); *C12N 2501/11* (2013.01); *C12N 2501/113* (2013.01); *C12N 2501/115* (2013.01); *C12N 2501/12* (2013.01); *C12N 2501/155* (2013.01); *C12N 2501/16* (2013.01); *C12N 2501/23* (2013.01); *C12N 2501/39* (2013.01); *C12N 2501/70* (2013.01); *C12N 2506/02* (2013.01)

(58) Field of Classification Search
CPC .................................................. C12N 5/0606
See application file for complete search history.

(56) References Cited

U.S. PATENT DOCUMENTS

2005/0003524 A1  1/2005  Gerlach
2006/0110369 A1  5/2006  Funatsu et al.

FOREIGN PATENT DOCUMENTS

WO   WO 2007/140968   12/2007
WO   WO 2008/083987   7/2008
WO   WO 2009/013254   1/2009

OTHER PUBLICATIONS

Lavon et al (Differentiation, 72(5): 230-8, 2004.*
Gerlach et al (Transplantation, 76(5): 781-786, 2003).*
Watanabe et al (Nature Biotechnology, 25(6): 681-686, 2007).*
Janne Jensen et al., *Human Embryonic Stem Cell Technologies and Drug Discovery*, 219(3) Journal of Cellular Physiology 513-519 (Mar. 10, 2009).
Satdarshan Monga et al., *Human fetal hepatocyte behavior in dynamic 3D perfusion culture bioreactors*, 3 Journal of Organ Dysfunction 183-192 (2007).
Sadhana Agarwal et al., *Efficient differentiation of functional hepatocytes from human embryonic stem cells*, 26(5) Stem Cells 1117-1127 (May 5, 2008).
Amit et al., *Clonally derived human embryonic stem cell lines maintain pluripotency and proliferative potential for prolonged periods of culture*, 227(2) Dev Biol 271-278 (2000).
Bar et al., *The biology of desmin filaments: how do mutations affect their structure, assembly, and organisation?* 148 J Struct Biol 137-152 (2004).
Cai et al., *Directed Differentiation of Human Embryonic Stem Cells Into Functional Hepatic Cells*, 45(5) Hepatology 1229-1239 (2007).
Chang-Qing et al., *Proliferative feeder cells support prolonged expansion of human embryonic stem cells*, 29 Cell Biol Int 623-628 (2005).
Chen et al., *Activin Signaling and Its Role in Regulation of Cell Proliferation, Apoptosis, and Carcinogenesis* 231(5) Exp Biol Med 534-544 (2006).
Conrad et al., *Generation of pluripotent stem cells from adult human testis*, 456 Nature 344-349 (2008).
Davie, *Inhibition of Histone Deacetylase Activity by Butyrate* 133(7) J. Nutr. 2485S-2493S (2003).
Dennis et al., *DAVID: Database for Annotation, Visualization, and Integrated Discovery*, 4 Genome Biol P3 (2003).
Evans et al., *Establishment in culture of pluripotential cells from mouse embryos*, 292 Nature 154-156 (1981).
Gentleman et al., *Bioconductor: open software development for computational biology and bioinformatics* 5(10) Genome Biology R80-R80.16 (2004).
Gerecht-Nir et al., *Bioreactor Cultivation Enhances the Efficiency of Human Embryoid Body (Heb) Formation and Differentiation*, 86(5) Biotechnol Bioeng 493-502 (2004).
Gerlach et al., *Use of primary human liver cells originating from discarded grafts in a bioreactor for liver support therapy and the prospects of culturing adult liver stem cells in bioreactors: a morphologic study*, 76(5) Transplantation 781-786 (2003).

(Continued)

*Primary Examiner* — Deborah Crouch
*Assistant Examiner* — Magdalene Sgagias
(74) *Attorney, Agent, or Firm* — Buchanan Ingersoll & Rooney PC

(57) ABSTRACT

The present invention relates to the use of 3D culturing systems for the derivation of hepatocyte-like cells from human pluripotent stem cells (hPS). In particular, the invention concerns the directed differentiation and maturation of human pluripotent stem cells into hepatocyte like cells in 3D hollow fiber capillary bioreactors.

15 Claims, 13 Drawing Sheets

(56) References Cited

OTHER PUBLICATIONS

Gerlach et al., *Bioreactor for a larger scale hepatocyte in vitro perfusion*, 58(9) Transplantation 984-988 (1994).
Golestaneh et al., *Pluripotent Stem Cells Derived From Adult Human Testes*, 18(8) Stem Cells and Development 1115-1125 (2009).
Hay et al., *Direct differentiation of human embryonic stem cells to hepatocyte-like cells exhibiting functional activities*, 9(1) Cloning Stem Cells 51-62 (2007).
Heng et al., *Factors influencing stem cell differentiation into the hepatic lineage in vitro*, 20 J Gastroenterol Hepatol 975-987 (2005).
Hines et al., *The Ontogeny of Human Drug-Metabolizing Enzymes: Phase I Oxidative Enzymes*, 300(2) J Pharmacol Exp Ther 355-360 (2002).
Itskovitz-Eldor et al., *Differentiation of Human Embryonic Stem Cells Into Embryoid Bodies Compromising the Three Embryonic Germ Layers*, 6(2) Molecular Medicine 88-95 (2000).
Jensen et al., *Human Embryonic Stem Cell Technologies and Drug Discovery*, 219(3) J Cell Physiol 513-519 (2009).
Kossack et al., *Isolation and Characterization of Pluripotent Human Spermatogonial Stem Cell-Derived Cells*, 27 Stem Cells 138-149 (2008).
Kubo et al., *Development of definitive endoderm from embryonic stem cells in culture*, 131(7) Development 1651-1662 (2004).
Kuhn et al., *A novel, high-performance random array platform for quantitative gene expression profiling* 14(11) Genome Res 2347-2356 (2004).
Lavon et al., *Differentiation and isolation of hepatic-like cells from human embryonic stem cells*, 72(5) Differentiation 230-238 (2004).
Levenberg et al., *Differentiation of human embryonic stem cells on three-dimensional polymer scaffolds* 100(22) Proc. Natl. Acad. Sci 12741-12746 (2003).
Li et al., *Culturing and differentiation of murine embryonic stem cells in a three-dimensional fibrous matrix*, 41 Cytotechnology 23-35 (2003).
Li et al., *Expansion of Human Embryonic Stem Cells in Defined Serum-Free Medium Devoid of Animal-Derived Products*, 91(6) Biotechnol. Bioeng 688-698 (2005).
Ludwig et al., *Derivation of human embryonic stem cells in defined conditions*, 24(2) Nat. Biotechnol. 185-187 (2006).
Pera et al., *Human embryonic stem cells: prospects for development*, 131(22) Development 5515-5525 (2004).
Przyborski, *Differentiation of human embryonic stem cells after transplantation in immune-deficient mice*, 23(9) Stem Cells 1242-1250 (2005).
Rambhatla et al., *Generation of Hepatocyte-Like Cells From Human Embryonic Stem Cells*, 12 Cell Transplant 1-11 (2003).
Rao, *Conserved and divergent paths that regulate self-renewal in mouse and human embryonic stem cells*, 275 Dev Biol 269-286 (2004).
Saeed et al., *TM4: A Free, Open-Source System for Microarray Data Management and Analysis*, 34(2) Biotechniques 374-378 (2003).
Sartipy et al., *The application of human embryonic stem cell technologies to drug discovery*, 12(17-18) Drug Discov Today 688-699 (2007).
Sauer et al., *Extracorporeal liver support based on primary human liver cells and albumin dialysis—treatment of a patient with primary graft nonfunction*, 39 J Hepatol 649-653 (2003).
Schuldiner et al., *Effects of eight growth factors on the differentiation of cells derived from human embryonic stem cells*, 97(21) Proc. Natl. Acad. Sci. 11307-11312 (2000).
Shih et al., *Identification of a candidate human neurohematopoietic stem-cell population*, 98(8) Blood 2412-2422 (2001).
Snykers et al., *In vitro differentiation of embryonic and adult stem cells into hepatocytes: state of the art*, 27 Stem Cells 577-605 (2009).
Soto-Gutierrez et al., *Differentiation of Human Embryonic Stem Cells to Hepatocytes Using Deleted Variant of Hgf and Poly-Amino-Urethane-Coated Nonwoven Polytetrafluoroethylene Fabric*, 15 Cell Transplant 335-342 (2006).
Takahashi et al., *Induction of Pluripotent Stem Cells From Adult Human Fibroblasts by Defined Factors*, 131 Cell 861-72 (2007).
Takahashi et al., *Induction of Pluripotent Stem Cells From Mouse Embryonic and Adult Fibroblast Cultures by Defined Factors*, 126 Cell 663-676 (2006).
Thomson et al., *Isolation of a primate embryonic stem cell line*, 92 Proc. Natl. Acad. Sci 7844-7848 (1995).
Wang et al., *Self-renewal of human embryonic stem cells requires insulin-like growth factor-1 receptor and ERBB2 receptor signaling*, 110(12) Blood 4111-4119 (2007).
Xie et al., *The differentiation of embryonic stem cells seeded on electrospun nanofibers into neural lineages*, 30(3) Biomaterials 354-362 (2009).
Bone et al., *A novel chemically directed route for the generation of definitive endoderm from human embryonic stem cells based on inhibition of GSK-3*, 124(12) Journal of Cell Science 1992-2000 (2011).
Ek et al., *Expression of drug metabolizing enzymes in hepatocyte-like cells derived from human embryonic stem cells*, 74 Biochemical Pharmacology 496-503 (2007).
Küppers-Munther et al., *Hepatocyte-Like Cells Derived From Human Embryonic Stem Cells Via Definitive Endoderm Display Drug Metabolising Activity*, 40(1) Drug Metabolism Reviews (2008)(Abstract Only).
Riedel et al., *Development of a fully defined animal component-free medium for efficient differentiation of human pluripotent stem cells to definitive endoderm*, http://www.stemcell.com/~/media/Technical%20Resources/1/7/E/F/F/Keystone%20Symposium%20%20STEMdiff%20Definitive%20Endoderm.pdf?la=en retrieved on Feb. 3, 2014.
Söderdahl et al., *Glutathione transferases in hepatocyte-like cells derived from human embryonic stem cells*, 21 Toxicology in Vitro 929-937 (2007).
Xie et al., *Three-Dimensional Flow Perfusion Culture System for Stem Cell Proliferation Inside the Critical-Size β-Tricalcium Phosphate Scaffold*, 12(12) Tissue Engineering 3535-3543 (2006).
International Search Report completed on Jan. 21, 2010, in corresponding Denmark Application Serial No. DK 200900751.

\* cited by examiner a

Samples:
- 00  Day 0
- Day 12, inoculation
- 02  Bioreactor day 26
- 2D control day 26

Samples:
- Day 0
- Day 12, inoculation
- Bioreactor day 26
- 2D control day 26

Fig. 11 - con't
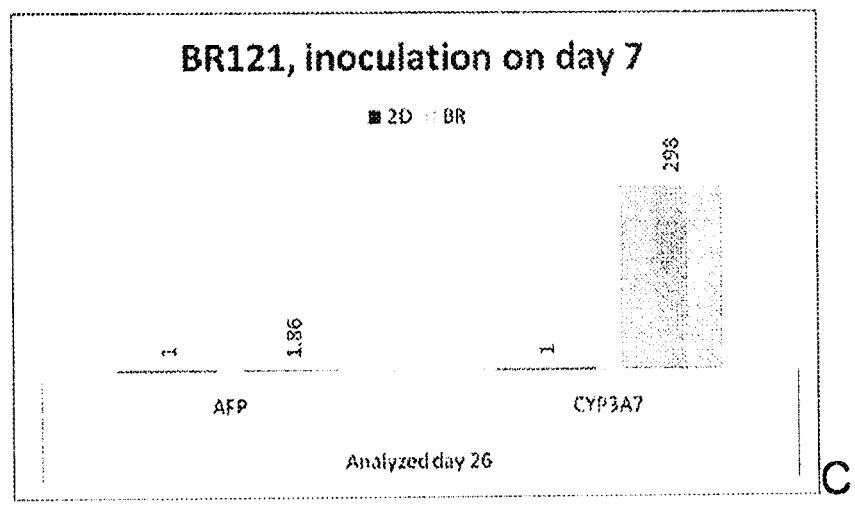
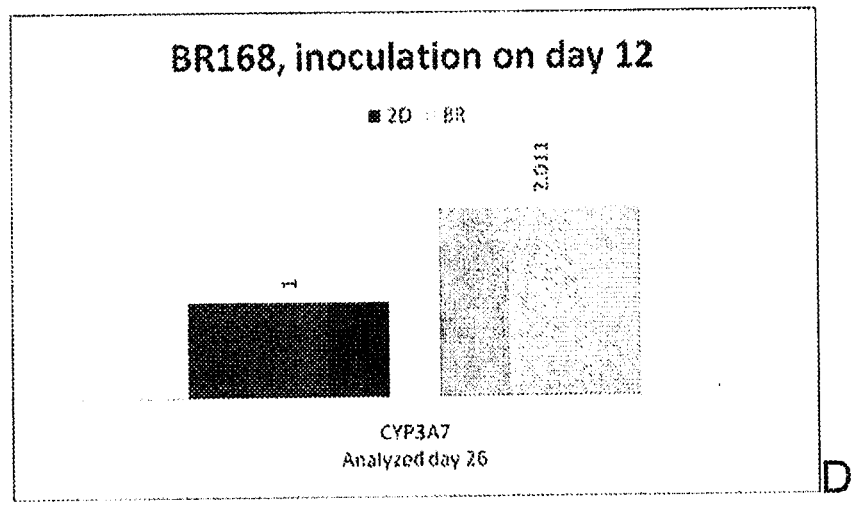

US 9,284,531 B2

DIFFERENTIATION OF HUMAN PLURIPOTENT STEM CELLS INTO CELLS EXPRESSING MATURE HEPATOCYTE MARKERS BY 2D AND BIOREACTOR CULTURE

CROSS-REFERENCE TO RELATED APPLICATIONS

This application is a U.S. National Stage pursuant to 35 U.S.C. §371 of International Patent Application PCT/EP2010/058679, filed on Jun. 18, 2010, and published as WO 2010/149597 on Dec. 29, 2010, which claims priority to U.S. Provisional Patent Application Ser. No. 61/218,140, filed on Jun. 18, 2009, and Danish Patent Application PA 2009 00751, filed on Jun. 18, 2009, all of which are incorporated herein by reference in their entireties for all purposes.

TECHNICAL FIELD

The present invention relates to the use of 3D culturing systems for the derivation of hepatocyte-like cells from human pluripotent stem cells (hPS). In particular, the invention concerns the directed differentiation and maturation of human pluripotent stem cells into hepatocyte like cells in 3D hollow fiber capillary bioreactors.

BACKGROUND OF THE INVENTION

For the development and implementation of stem cell-based applications in regenerative medicine and applied research, such as drug screening or toxicology testing, large numbers of cells with well defined characteristics are needed. Therefore culture systems are required that allow the directed reproducible differentiation of hPS into mature hepatocyte like cells with a high yield and purity.

DESCRIPTION OF THE INVENTION

The present invention relates to a method for obtaining hepatocyte-like cells, the method comprising
  i) inoculation of hPS or hepatic precursor cells in a bioreactor
  ii) perfusing the bioreactor with one or more culture media for a time period of from 10 to 50 days to obtain hepatocyte-like cells.

An aspect of the invention, the invention relates to hepatic tissue-like 3D structures comprising hepatocytes-like cells obtained by a method for obtaining hepatocyte-like cells, the method comprising
  i) inoculation of hPS or hepatic precursor cells in a bioreactor
  ii) perfusing the bioreactor with one or more culture media for a time period of from 10 to 50 days to obtain hepatocyte-like cells.

In a further aspect of the invention, present invention relates to the use of the cells obtained by a method for obtaining hepatocyte-like cells, the method comprising
  i) inoculation of hPS or hepatic precursor cells in a bioreactor
  ii) perfusing the bioreactor with one or more culture media for a time period of from 10 to 50 days to obtain hepatocyte-like cells,
for therapeutic purposes, in drug discovery, pharmaceutical formulations, toxicity testing or in regenerative medicine.

In a further embodiment, the invention relates to the use of a bioreactor for differentiating hPS cells or hepatic precursors towards a hepatic cell fate.

INTRODUCTION

Current 3D suspension culture model approaches to differentiation using aggregates or microcarriers are limited in central mass exchange. By offering perfusion-based dynamic culture conditions with continuous medium exchange and decentral oxygenation at controllable gas tensions in larger cell masses, the 3D perfusion four-compartment capillary membrane bioreactor technology enables using the advantages of both culture concepts. In addition, application of differentiation regimes in a closed system, suitable for good manufacturing practice (GMP) conditions is possible. The technology allows varying but controllable medium- and system parameters including, e.g., oxygen tensions, gas factor application, medium factor gradients, or generating physical stimuli such as flow and pressure on the cells.

Culture of hPS Cells in Bioreactors

For the development and implementation of stem cell-based applications in regenerative medicine and applied research, such as drug screening or toxicology testing, large numbers of cells with well defined characteristics are needed. Therefore culture systems are required that allow a directed reproducible differentiation of undifferentiated human embryonic stem cells into mature hepatocytes with a high yield and purity.

The most commonly used culture and differentiation methods typically utilize 2D culture systems in the form of plastic dishes, which represent static open systems with discontinuous medium exchange, which leads to periodical changes of the culture environment in form of accumulation of metabolites and reduction of nutrients in the culture medium between medium changes. Furthermore these 2D cultures are labor intensive because they require extensive manual intervention and therefore make handling of larger cell numbers impractical.

Differentiation of hPS Cells in Bioreactors

Hepatic differentiation of hESC studies by Soto-Gutierrez et al. indicate that a more complex environment, using complex matrix structures or co-culture with nonparenchymal cells supports hepatic differentiation of hESC (Soto-Gutierrez et al. 2006). Levenberg et al. showed that in biodegradable scaffolds of PLGA-poly(lactic-co-glycolic acid) and PLLA-poly(L-lactic acid) seeded with ES cells or EBs induction of hepatic tissue-like structures was possible by treatment with activin A and IGF (Levenberg et al. 2003). Baharvand et al. reported enhanced hepatic differentiation of hESC in 3D collagen scaffolds (Baharvand et al. 2006). Therefore use of perfused bioreactors providing a 3D culture environment could lead to more efficient and scalable methods for embryonic stem cell differentiation.

A novel approach is the usage of hollow fiber bioreactors for embryonic stem cell expansion and differentiation. Hollow fiber capillary membrane bioreactor technologies enable dynamic perfusion culture conditions and allow increasing the cell density as stem cells find it in the natural tissue. In addition scale-up for larger cell masses is possible. However, the typical two-compartment bioreactor devices (e.g. FiberCell Duet, FiberCell systems, Inc.,), with a cell compartment around a bundle of surrounding capillaries, nutrition mainly via diffusion and external oxygenation, are limited by non-uniform mass exchange with substrate gradient distances along decimeters of capillary length.

In the 3D multicompartment technology developed by Gerlach et al. (Gerlach et al. 1994), another medium- and an additional oxygenation membrane compartment were added to the typical two-compartment devices. Interweaving the four compartments to form repetitive units enables scalability of the bioreactors, provides decentralized medium perfusion and -substitution, while mass exchange is enhanced and gradient distances are reduced. The concept is based on culturing cells in a closed and thus good manufacturing practice (GMP) suitable culture environment, which facilitates biotechnological applications, as well as potential clinical translation of the results. Initial clinical studies using primary porcine or human liver cells cultured in bioreactors demonstrated the feasibility of clinical extracorporeal liver support with the system (Sauer et al. 2003). In addition it was shown that primary cells can create their own typical microenvironment in such in vitro culture models, including formation of liver-like tissues with neo-sinusoids and biliary structures. Adult stem cells could benefit from parenchymal/nonparenchymal cell co-culture in such systems for the creation of anorgano-typical microenvironment (Gerlach et al. 2003).

Because of their unique characteristics hPS cells hold great potential as a cell source for applications in basic science, pharmacological drug screening, toxicity testing and cell based therapies in regenerative medicine. It has been demonstrated that under certain growth conditions, hPS cells are able to differentiate into a wide variety of somatic and extraembryonic tissues in vitro (Pera et al. 2004). Accordingly, hPS and in particular hES/hBS cells make it possible to investigate the molecular pathways and control mechanisms that control the fate of cells during early embryonic development, which was not possible before due to the inaccessibility of human embryos to research. Possible clinical applications of hPS cells can be seen in the provision of stem cell-derived cell preparations for cell-based therapies in patients with organ defects like hepatic insufficiency, spinal cord injuries or myocardial defects. The areas of possible utilization of hPS cell derived differentiated cells in drug discovery can be seen in pre-clinical activities like target identification and validation, screening of compound efficacy and safety assessment studies (Sartipy et al. 2007). Regarding embryotoxicity testing, undifferentiated hPS cells also provide a novel tool for the development of better test systems.

Development of the Mammalian Liver

The liver is one of the first organs to develop in the embryo and it rapidly becomes one of the largest organs in the fetus. The liver develops from the definitive endodermal epithelium of the embryonic foregut. Initially suppression of Wnt and fibroblast growth factor signaling (FGF4) in the foregut is necessary for induction of liver development. Then FGFs from the cardiac mesoderm and bone morphogenic proteins (BMPs) from the septum transversum mesenchyme induce spatial restricted cell proliferation which leads to thickening of the endodermal layer. The cells then emerge from the epithelium and begin to migrate into the septum transversum. The mass of cells emerging from the endoderm and concentrating in the septum transversum is referred to the liver bud. Interactions with endothelial cells in this stage of organogenesis are crucial for this early budding phase. The hepatic endoderm cells are quite immature in terms of function and morphology during this time and are now referred to as hepatoblasts. Cords of hepatoblasts from the liver bud penetrate the mesoderm, intermingling with the vitelline and umbilical veins, which anastomose near the liver bud to form a capillary bed. These transitions establish the liver's sinusoidal architecture, which is critical for organ function and sets the stage for the liver to support fetal hematopoiesis. The hematopoietic stem cells that migrate into the liver bud secrete oncostatin M (OsM) that induces further hepatic maturation together with glucocorticoids. Other cell types that contribute to the embryonic liver mass are endothelial cells that surround the hepatic sinusoids, the Kupffer cells, and hepatic stellate cells. The hepatocyte growth factor (HGF) produced by these cells is important for the full functional hepatic maturation. In these later stages of liver differentiation Wnt signaling no longer inhibits but promotes growth and differentiation. The lack of causal liver therapies and the insufficient availability of donor organs for liver transplantation create a demand for the development of new cell-based liver therapies. Transplantation of stem cells capable of proliferation and differentiation to replace the injured tissue could replace whole-organ transplantation in some clinical indications.

Hepatic Differentiation of hPS Cells In Vitro

Studies on strategies for direction of hepatic differentiation of HPS cells and in particular hES/hBS cells in vitro led to the identification of several cytokines, growth factors and non-protein compounds that have an effect on hepatic differentiation (reviewed in Heng et al. 2005; Snykers et al. 2008). The growth factors include activin A, BMP2 and -4, epidermal growth factor (EGF), FGF1, -2 and -4, HGF, insulin and OsM. The non-protein factors include dexamethasone (DEX), dimethylsulfoxide (DMSO), nicotinamide and sodium butyrate. The key to the effect of each differentiation factor is the timing, concentration and combination with other factors. To characterize the hPS derived hepatocyte like cells various markers and functional test have been utilized (reviewed by Snykers et al. 2008). The markers examined by immunocytochemistry, polymerase chain reaction (PCR) or enzyme-linked immunosorbent assays (ELISA) included secretion of plasma proteins like alpha fetoprotein (AFP), albumin (ALB) and urea, cytokeratines (CK8, CK18, CK7, CK19) and various hepatocyte specific enzymes like alpha-1-antitrypsin ($\alpha$1AT), dipeptidyl peptidase IV (DPPIV) and cytochrome P450 isoenzymes. The expression of hepatocyte specific functions has been examined for example by detection of the storage of glycogen and metabolism of various test substrates specific for cytochrome P450 isozymes.

The first published protocols describing hepatic differentiation of hPS cells applied as a first step, the induction of EBs followed by adherent culture using various growth factors to enrich for hepatic cells (Lavon et al. 2004). In these studies only very low yields and purity of the final cell populations have been reported. The most successful differentiation protocols described so far try to mimic organ development of the liver starting with induction of definitive endoderm (DE) differentiation of the hESC (Cai et al. 2007). Basically, high concentrations of activin A together with low serum/insulin conditions, to provide reduced insulin/insulin-like growth factor (IGF) signaling, are applied for DE differentiation with yields of up to 80% DE cells (Kubo et al. 2004). This is followed by sequential treatment with FGFs, BMPs, HGF, OsM/DEX. With this approach, described yields of hepatocyte like cells were about 50%. Other protocols include the treatment of hESC's with sodium butyrate (NaB) that inhibits histone deacetylase activity (Davie 2003). Application of this epigenetic differentiation agent in the first step of a differentiation protocol yielded 10% hepatic cells from hESC and a purity of up to 70% of the final cell populations (Rambhatla et al. 2003). Combination of NaB treatment with DE induction by activin A showed promising results, attaining a yield of hepatic cells of up to 70% (Hay et al. 2008).

In summary the yield, purity and maturational degree of hESC derived hepatic cells derived by the current approaches are still suboptimal and therefore novel methods are needed.

The present invention addresses these problems by providing a method for obtaining hepatic cells from hPS such as e.g. hBS cells by inoculating these, or DE-cells derived therefrom in a bioreactor in which they are subjected to differentiation.

Application of hPS Derived Hepatocytes

A future clinical use of hPS derived hepatocytes can be seen in their application for cell transplantation in patients with hepatic insufficiency, e.g. in the case of certain genetic defects or acute or chronic liver failure (Ito et al. 2009). Transplantation of stem cell derived hepatocytes could replace whole-organ transplantation in some clinical indications, and—when using immunocompatible cells—make dispensable the need of immunosuppressive therapy. A further therapeutic option can be seen in the provision of a reliable human cell source for extracorporeal liver support, to bridge the liver function until transplantation or until regeneration of the patient's organ, which would also solve the existing problem of cell availability for extracorporeal liver devices. Moreover, extracorporeal systems could also provide an interesting therapeutic option to bridge the liver function after cell transplantation until the applied cells show sufficient liver specific metabolic performances. Potential applications in pharmaceutical research are the use of hPS cell derived hepatocytes for the development of novel hepatic assays needed for drug discovery. This could overcome the poor predictive power of existing in vitro tools and lead to new human cell based test systems that will allow more reliable and relevant testing in the preclinical phase and hinder weak lead candidates to enter clinical phases (Jensen et al. 2009).

The invention also relates to the use of a bioreactor for the production of conditioned medium. The standard method for the production of conditioned medium (CM) is incubation of culture medium for 24 hours in standard culture vessels seeded with inactive MEF feeder cells at a high density. This method is labour intensive and space consuming, because large numbers of feeder cells have to be produced that can only be used for a limited amount of time for medium conditioning until they loose their activity. Therefore the production of larger volumes of CM is limited by the poor scalability of this method. An alternative approach to the use of CM for culture hBS cells is the use of defined culture media. Several defined medium formulations have been described for feeder independent culture of hESC (Li et al. 2005; Ludwig et al. 2006). While the use of defined medium has several advantages like the possibility to culture hBS cells under conditions completely free of animal derived substances, its major disadvantage is that these media formulations include significant amounts of expensive supplements like recombinant cytokines and growth factors.

As outlined above, the present invention relates to a method for obtaining hepatocyte-like cells, the method comprising i) inoculation of hPS or hepatic precursor cells in a bioreactor ii) perfusing the bioreactor with one or more culture media for a time period of from 10 to 50 days to obtain hepatocyte-like cells.

The hepatocyte-like cells may be in the form hepatic tissue-like 3D structures comprising hepatocyte-like cells, hence as clustered together in 3D aggregates. The hPS cells may be but are not limited to human embryonic stem cells or induced pluripotent stem (iPS) cells as described in the definitions. The hepatocyte hepatocyte precursor cells may be definitive endoderm (DE) or not resembling DE, or the hepatocyte precursor cells may have the characteristics of fetal endoderm or hepatic endoderm. The bioreactor as referred to above may be a hollow fibre capillary bioreactor, optionally provided with membrane compartments. The bioreactor may comprise two or more capillary systems and one or more hollow fibre membrane. Further, the bioreactor may comprise means for perfusion of culture medium through a capillary system and means for gas exchange in the capillary system, optionally the perfusion of growth medium takes place through the capillary systems, and gas exchange takes place via a hollow fibre membrane system. The capillary systems and one or more hollow fibre membranes may be configured to form independent interwowen fibre capillary membrane systems integrated into a housing.

The hPS cells may be seeded in step i) and the perfusion may follow the following scheme, provided that at least three of steps 2-6 are included:

| Step | Period | Medium name |
| --- | --- | --- |
| 1 | From 1 to 7 days, notably from 1 to 3 days | hPS culture medium or IDM-A |
| 2 (optional) | From 1 to 10 days, notably from 1 to 5 days | DM-A or IDM-B |
| 3 (optional) | From 1 to 4 days, notably from 1 to 3 days | DM-B or PM-A |
| 4 (optional) | From 1 to 10 days, notably from 1 to 7 days | DM-C or VHM-A |
| 5 (optional) | From 1 to 20 days, notably from 3 to 9 days | DM-D or VHM-B |
| 6 (optional) | 10 days or more such as 15 days or more, notably from 10 to 50 days | DM-E or MM-A |

Alternatively, all of the steps 1-6 may be included.

As detailed herein, the culture medium DM-A may comprises a growth medium, and one or more of the components: Activin A, bFGF, Glutamax-I.

As detailed herein, culture medium DM-B may comprise growth medium such as RPMI Advanced medium or the like, and one or more of the components: Activin A, bFGF, GLutamax-I, FCS.

As detailed herein, culture medium DM-C may comprise a growth medium such as RPMI Advanced medium or the like, and one or more of the components: bFGF, aFGF, BMP2, BMP4, Glutamax-I, FCS.

As detailed herein, culture medium DM-D comprises a hepatic culture medium such as Williams medium E or the like, and one or more of the components: BSA, Ascorbic acid, Glutamax-I, D-Galactose/D-sorbitol, Hydrocortisone, Insulin, Transferrin, bFGF, EGF, HGF.

As detailed herein culture medium DM-E comprises a hepatic culture medium such as Williams medium E or the like, and one or more of the components: BSA, Ascorbic acid, Glutamax-I, Dexametasone, D-Galactose/D-sorbitol, Hydrocortisone, Insulin, Transferrin, bFGF, EGF, HGF, Oncostatin M.

All of the culture media listed may optionally comprise a rho kinase inhibitor such as BIO or any variants of BIO.

Prior to step i), the bioreactor may be inoculated with inactivated feeder cells. Such feeder cells may be, but are not limited to hFF or MEF cells.

Further, the bioreactor may be co-inoculated in step i) with hBS cells and feeder cells or DE cells and feeder cells, whichever is relevant.

Further, hepatic precursor cells, such as DE cells, may be seeded in step i) and steps 1 and 2 (marked with bold) of the table below may be omitted.

| Step | Period | Medium name |
|---|---|---|
| 1 | From 1 to 7 days, notably from 1 to 3 days | hPS culture medium or IDM-A |
| 2 (optional) | From 1 to 10 days, notably from 1 to 5 days | DM-A or IDM-B |
| 3 (optional) | From 1 to 4 days, notably from 1 to 3 days | DM-B or PM-A |
| 4 (optional) | From 1 to 10 days, notably from 1 to 7 days | DM-C or VHM-A |
| 5 (optional) | From 1 to 20 days, notably from 3 to 9 days | DM-D or VHM-B |
| 6 (optional) | 10 days or more such as 15 days or more, notably from 10 to 50 days | DM-E or MM-A |

As outlined above the present invention relates to 3D-culturing of hPS cells such as hESC/hBSC and in particular culturing of said cells in a multicompartment bioreactor system as a novel in vitro system that supports growth and differentiation of hPS cells, with emphasis on directed hepatic differentiation. Results indicate that the 3D environment of the bioreactor constitutes a more in vivo-like environment than standard 2D culture systems and therefore enables improved growth and differentiation of hPS cells compared to these systems.

Further, the invention relates to a method wherein the initial differentiation of the cells is performed in a conventional 2D environment prior to seeding the cells in the bioreactor. Interestingly the inventors of present invention have found that by initiating the differentiation of the hPS towards definitive endoderm in a 2D environment and subsequently seeding the initially differentiated cells into the bioreactor provides more pure cultures. After initial differentiation to definitive endoderm in 2D cultures, the cells are seeded in the bioreactor. Examples of initial 2D differentiation and subsequent inoculation and further differentiation in the bioreactor are provided in table 2, and table 3-5.

Accordingly, the initially differentiated cells may be seeded in the bioreactor from day 3 to day 20, such as e.g. day 8 to 12, such as e.g. day 11 or 12.

Further to the aspects above, differentiation of hPS cells towards a hepatic cell fate may be further stimulated by activin A, optionally a RHO kinase inhibitor and high growth factor levels. The cells may be seeded into the bioreactor at a given time point (day 12 for experiment shown in Table 3, days 7 or 11 for experiment shown in Table 4) and allowing further differentiation and maturation to occur.

As described herein, the inventors have found that by applying a 3D bioreactor hepatic differentiation of hPS is efficiently directed towards a hepatic cell fate. Detailed protocols applicable for facilitating efficient differentiation of hPS towards a hepatic cell fate is described in detail below and in particular in the examples herein. As illustrated herein, differentiation of hPS cells may be facilitated with or without the use of feeder cells such as e.g. mouse embryonic feeder cells (MEF) or human foreskin fibroblasts (HFF). Further, the growth media may comprise any suitable growth medium including any of the growth media described herein as hESC culture medium, and DM-A, DM-B, DM-C, DM-D and DM-E. The invention presently presented therefore also encompasses any amendments to the growth medium compositions (e.g. removal or addition of growth medium components) that, according to the person skilled in the art are obvious to apply to amend or replace the growth and differentiation media presented herein. Similarly, any changes in the incubation time, flow rates or culture conditions due to e.g. delayed cell maturation or stage specific growth factor addition are within the scope of present invention, as such minor adjustments are to be considered obvious applications of the present invention.

Before initial cell inoculation, the bioreactor may be conditioned by recirculation of a suitable growth medium for a given period of time, e.g. 24-72 hours. Any suitable medium and flow-rate may apply, including any medium used for differentiating the cells, at any stage of differentiation. Alternatively, the conditioning may be minimized thereby allowing almost immediate seeding of the cells in the bioreactor.

The flow applied in the bioreactor may depend on several factors such as e.g. the stage of differentiation, inoculation size, maturation of the cells, viscosity of the growth medium etc. The flow of the air/CO2 mixture in the gas compartment may be from 0.2 ml/min to 120 ml/min, such as 10 to 80 ml/min, such as 30 ml/minute.

According to the present invention, cells may be seeded in the bioreactor at any suitable concentration or number. As non-limiting example, from $1\times10^6$ to $10\times10^8$ cells, such as $2.5\times10^7$ to $10\times10^7$ cells may be seeded in the bioreactor.

The pH, partial pressures of oxygen (pO2) and carbon dioxide (pCO2) and the acid/base status may be periodically measured. The air/CO2 mixture may be varied to maintain a specific pH value and partial pressure of the O2 and CO2. Accordingly, the air/CO2 mixing ratio may be adjusted to maintain a stable pH between 5 and 9, such as eg. 7.2 or 7.3.

The bioreactor may be seeded with feeders, such as e.g. MEF cells before seeding the hPS in the bioreactor. For example the feeder cells may be seeded 5 to 0 days such as e.g. 1 to 4 days before seeding the hPS cells in the bioreactor, such as 2 days before seeding the hPS cells in the bioreactor.

After seeding the hPS cells in the bioreactor, the growth media may be changed after defined intervals. The differention media composition may be changed every 1 to 15 days, depending on cell differentiation speed and cell maturation. For inspiration with regards to growth media composition, feed rates and intervals between changing the growth medium composition, please see Table 2 herein.

Before, during and after differentiaion in the bioreactor, metabolic parameters may be monitored. This may be done by measuring soluble factors in the medium outflow and in the recirculating medium. Parameters may encompass any relevant and measurable parameters such as factors comprising: α-fetoprotein (AFP), alkaline phosphatase (AP), alanine transaminase (ALT), aspartate transaminase (AST), beta-human chorionic gonadotropin (β-hCG), c-peptide, carcinoembryonic antigen (CEA), cytokeratin fragment 19 (Cyfra 21-1), erythropoetin, estradiol, follicle stimulating hormone (FSH), factors II-V-X-XIII, fibrinogen, gamma-glutamyl-transferase (GGT), glucose, lactate, lactate dehydrogenase (LDH), luteinizing hormone, neuronspecific enolase (NSE), osmolality, osteocalcin, pseudocholinesterase (PCHE), pre-albumin progesterone, prolactin, S-100, thyroid-stimulating hormone (TSH), tissue plasminogen activator (TPA), transferrin, glutamine, glutamate, glucose, lactate, ammonium, pH, sodium (Na+), potassium (K+), Activin A, insulin and albumin, urea, Galactose and sorbitol. Any applicable method for measuring said compounds may be applied. The production or consumption rate of each substance may be calculated, e.g. per day by multiplying the actual waste volume of the day by the difference between the substance concentration in the feed medium and that in the waste medium.

Further to the parameters or substances above, the metabolic activity of the cultures may be tested. As example, the ability of the bioreactors to metabolize phenacetin, diclophenac and midazolam via the phase I cytochrome (CYP) P450 enzymes CYP1A2, CYP2C9 and CYP3A4, may be tested. The test may be performed at any stage of differentiation in order to e.g. adjust the culture conditions and growth media compositions during differentiation. However, the test of metabolic activity may be most relevant at a relatively late stage of differentiation when the cells are fully or partly directed towards a hepatic cell fate or differentiated to hepatocytes or hepatocyte-like cells. As example, the test may be performed between day 30 and 60 of differentiation, such as e.g. at days 40 and 47 after inoculation of the cells.

A CYP P450 activity test may as example be performed according to the scheme:

| CYP1A2: | Phenacetin -> | Acetaminophen |
| CYP2C9: | Diclofenac -> | 4'OH diclofenac |
| CYP3A4: | Midazolam -> | 1'OH midazolam |

The test substances may be injected into the recirculating medium to get the following concentrations at the beginning of the test: 0.5 to 10 µM such as e.g. 3 µM Midazolam, 1 to 25 µM such as e.g. 9 µM Diclophenac and 2-60 µM such as e.g. 26 µM Phenacetin. The bioreactor could then be operated in recirculation mode for 24 hours. Samples from the recirculation could then be taken before starting the experiment and after 1, 4, 8 and 24 hours and analyzed for the metabolites of the test substances by e.g. liquid chromatography/mass spectrometry (LC/MS).

Isolation of RNA, cDNA synthesis, array hybridisations and data analysis may be performed by any method known in the art. Additionally histochemical and immunihistological analyses as well as electron microscopic analysis of the cells and growth medium may be performed with any equipment and reagent forming part of the available toolbox of the person skilled in the art.

In line with the details outlined above, the cells obtained may be analysed with respect to differentiation specific markers. In one example four groups of markers may be measured (Hepatic genes, markers for fetal/immature hepatocytes, transporters and markers for undifferentiated cells.), with measurement time points consisting of Day 0, Inoculation day, and bioreactor shutdown day. For comparative purposes, control groups comprising cells obtained after 2D culturing only may be included and analysed accordingly.

A further aspect of the invention relates to the use of the bioreactor for production of conditioned medium for culture of undifferentiated hPS cells.

The inventors of present invention have observed that the presence of inactive HFF delays the start of hESC differentiation until the HFF loose their activity. The pluripotency supporting activity of the HFF could be correlated with their production of activin A. To further examine the behaviour of the HFF feeder cells several experiments only with HFF were carried out in 2D cultures and in two bioreactors.

In one experiment, the bioreactor is inoculated with active HFF that will be cultured in medium supplemented with serum and bFGF to stimulate HFF proliferation. Increase of the cell number is monitored by the levels of glucose consumption and lactate production. When a sufficient cell number is reached culture medium is changed to hBS medium for conditioning. Optimal medium exchange rates have to be determined for example measuring activin A and glucose concentrations in the conditioned medium as quality control parameters. A low glucose level might indicate the demand for increasing the medium feed rate and a low activin A level might be a sign for insufficient conditioning unsuitable to promote hESC pluripotency.

Observations from 2D and 3D experiments show that activin A production is stimulated by bFGF in combination with medium containing serum replacer. In medium supplemented with serum, bFGF did not stimulate activin A production but exhibited a strong mitogenic effect on active HFF. This effect was also observed in bioreactor experiment HFF-1 characterized by increasing levels of glucose and lactate metabolism upon bFGF addition to the medium. This mitogenic effect was not observed in the bioreactor experiment HFF-2, in which medium supplemented with serum replacement was used. In this experiment glucose and lactate metabolism stayed on a constant level which shows that the cells did not proliferate.

Accordingly the observations illustrates the bioreactor technology could be applied in the production of conditioned medium that is needed for feeder free expansion of undifferentiated hPS cells.

Cultivation of HFF in a bioreactor to produce CM could be an alternative to conventional methods. It would enable high cell densities of human feeder cells in a scalable system that allows automatic control of the culture parameters and defined rates of medium in and outflow. Therefore standardization of the conditioning process will be possible resulting in an increased quality of the produced CM compared to manual methods. One further advantage when using the bioreactor would be the possibility to use active feeder cells because it has been shown that active feeder cells also support maintenance of pluripotency (Xie et al. 2005). This would decrease the number of active feeder cells that have to be produced in conventional 2D cultures for initial bioreactor inoculation.

Further, the bioreactor containing hESC derived differentiated cells may be used as an extracorporeal device in medical therapies and as an alternative to animal testing in applications like for example pluripotency testing by teratoma formation and drug metabolism studies.

Alternatively, the present invention may be used as a scalable system for the production of large numbers of undifferentiated or differentiated hBS cells needed for basic research, pharmacological drug screening and cell based clinical applications. However, for these applications, methods as the methods disclosed herein and leading to cell preparations highly enriched for specific cell types are key prerequisites.

Hence, the invention also relates to hepatic tissue-like 3D structures comprising hepatocytes-like cells obtained by a method disclosed herein.

The hepatocyte like cell or a hepatic tissue-like 3D structure comprising hepatocyte-like cells according to present invention may express elevated levels of one or more hepatic marker genes or hepatic transporter genes.

Examples of such hepatic marker genes may be selected from a list comprising Albumin, CYP1A2, CYP2C9, CYP3A4, CYP7A1, TAT & UGT2B7 and the expression of the one or more hepatic marker may typically resemble the expression of the hepatic marker genes as listed as Sample: Bioreactor day 26 in FIG. 7 herein. It is hereby contemplated that FIG. 7 form part of the general inventive concept of present invention.

Further the hepatocyte like cell or a hepatic tissue-like 3D structures comprising hepatocyte-like cells according to present invention may express elevated levels of hepatic transporter genes. The genes may be selected from the list comprising ABCC2/MRP2, FABP1, OATP2, OCT-1. The expression of one or more the hepatic transporter genes may resemble the expression pattern as listed as sample: Bioreactor day 26 in FIG. 9 herein. It is hereby contemplated that FIG. 9 form part of the general inventive concept of present invention.

An aspect of the invention relates to an in vitro derived hepatocyte-like cell in a bioreactor provided with membrane compartments. In one aspect, the cell may have been differentiated from a hPS cells or a hepatocyte precursor to a hepatocyte-like cell in the bioreactor.

The bioreactor as referred to above may be a hollow fibre capillary bioreactor, optionally provided with membrane compartments. The bioreactor may comprise two or more capillary systems and one or more hollow fibre membrane. Further, the bioreactor may comprise means for perfusion of culture medium through a capillary system and means for gas exchange in the capillary system, optionally the perfusion of growth medium takes place through the capillary systems, and gas exchange takes place via a hollow fibre membrane system. The capillary systems and one or more hollow fibre membranes may be configured to form independent interwowen fibre capillary membrane systems integrated into a housing.

Further, the bioreactor hepatocyte-like cell or hepatic tissue-like 3D structures comprising hepatocyte-like cells in the bioreactor, may be growing in the presence of a cell survival factor, such as an inhibitor of ROCK Rho kinase.

Present invention also relates to a method for producing conditioned medium, the method comprising the steps of
  a) inoculation of feeder cells in a bioreactor
  b) growing the feeder cells As detailed above, the bioreactor as referred to above may be a hollow fibre capillary bioreactor, optionally provided with membrane compartments. The bioreactor may comprise two or more capillary systems and one or more hollow fibre membrane. Further, the bioreactor may comprise means for perfusion of culture medium through a capillary system and means for gas exchange in the capillary system, optionally the perfusion of growth medium takes place through the capillary systems, and gas exchange takes place via a hollow fibre membrane system. The capillary systems and one or more hollow fibre membranes may be configured to form independent interwowen fibre capillary membrane systems integrated into a housing.

Yet a further aspect of the invention, relates to the use of the cells obtained by any of the methods herein for therapeutic purposes, in drug discovery, pharmaceutical formulations, toxicity testing or in regenerative medicine.

As disclosed herein, the inventors of present invention have found that the 3D perfusion culture technology represents a promising tool for stem cell expansion and differentiation at high densities in a highly controlled environment. And could possibly be used to for the production of embryonic or pluripotent stem cell-derived cell preparations for trans-plantation in patients with hepatic insufficiency, e.g. in the case of certain genetic defects or acute to chronic liver failure. A further therapeutic option can be seen in the application of the bioreactor technology for extracorporeal liver support intended to bridge the liver function until transplantation or until organ regeneration by using hESC derived liver cells as a human cell source. Extracorporeal systems could also provide a useful therapeutic option to bridge the liver function after stem cell transplantation until the applied cells show sufficient functional performances. Finally stem cells and stem cell derived differentiated cells expanded and maintained in the bioreactor system could also be used to produce regenerative substances that stimulate the endogenous regeneration process in vivo.

Hence the cells or 3D cell structures obtained by a method described herein may be used for drug discovery, toxicity testing, hepatotoxicity testing or for studying drug transporters, drug metabolizing enzymes, hepatogenesis, early hepatogenesis, hepatocyte maturation or human hepatoregenerative disorders.

Furthermore cells or 3D structure of cells obtained after growth in the bioreactor and according to any of the methods described herein may be applied as a medicament or for the manufacture of a composition for the prevention and/or treatment of pathologies and/or diseases caused by tissue degeneration, such as, e.g., the degeneration of liver tissue and/or auto immune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e.g. pharmaceutical drugs; and tumor removal in patients suffering from e.g. hepatocellular carcinoma. Additionally the cells or 3D structures hereof may be used for the manufacture of a composition for the treatment and/or prevention of metabolic pathologies and/or diseases or as a method for screening a compound for its ability to modulate hepatocellular function, comprising exposing the cells grown in the bioreactor according to any of the methods disclosed herein, to the compound, determining any phenotypic or metabolic changes in the cells that result from contact with the compound.

The possibility of an insufficient histocompatibility of hPS derived cell and safety aspects regarding an inherent risk of tumour formation by contaminating undifferentiated hESC in transplanted cell preparations are also discussed. Therefore alternative cell sources are examined with the goal to derive histocompatible, pluripotent cells that could solve these problems. The bioreactor technology could be applied in the characterization and the comparison of the candidate cell types with hESC which at the moment represent the gold standard.

As part of present invention two pilot experiments on the directed hepatic differentiation of hPS cells (hPSC) in the bioreactor were initially performed to assess feasibility. The two bioreactor experiments (HepDiff-1 and HepDiff-2) differed only in the additional inoculation of inactivated MEF into one of the bioreactors. The differentiation protocol used was developed for hPSC cultured on MEF (see Tables 1 and 2, also FIG. 3). Following inoculation, the hPSC were cultured during the first four days of the experiments in standard culture medium which contains serum replacement (DM-A, see Table 2). This initial step was chosen to allow the undifferentiated cells to adapt to the new culture environment and to start differentiation when the HFF lose their differentiation inhibiting activity but before the onset of spontaneous differentiation. The step was chosen based on three observations: Firstly in preliminary bioreactor experiments an increased rate of cell death, indicated by a peak of LDH, was observed after cell inoculation. This increased cell death might be due to the process of cell harvesting from the 2D cultures, the inoculation process itself and/or induced by the changed environment of bioreactor to that the cells have to adapt to. Secondly the differentiation conditions applied in the following step have a high selection pressure on the cells. Therefore applying these conditions directly after cell inoculation is another stress factor for the cells and could lead to increased cell death. Thirdly the culture length of four days before start of directed differentiation was chosen based on the observation that in neither of the previous experiments differentiation markers were detected in this time period and HFF activity, measured by their activin A production, constantly decreased.

Bioreactor HepDiff-2, in which additional inactive MEF were inoculated showed a much higher metabolism of glucose and lactate compared to HepDiff-1 without feeders (FIG. 4). This indicates that the presence of inactivated MEF is cell protective for the hESC and results in a better cell survival after inoculation. A lower cell survival in the absence of feeders becomes also evident when comparing AFP production and CYP450 activity in the bioreactors. The levels of these parameters were about eight times lower in the bioreactor HepDiff-1 without feeders compared to bioreactor HepDiff-2 with feeder cells (FIG. 5). Production of AFP was observed in both bioreactors and started at about experimental day 17. This can be interpreted as a sign of early hepatic differentiation presuming preceding successful DE differentiation of the cells. AFP is a marker for differentiation of DE cells into hepatoblasts, the major cell type of the fetal liver, but can also indicate differentiation of the undifferentiated cells into primitive endodermal cells. Significant metabolism of phenacetin by CYP1A1/1A2 was detected in the bioreactors (FIG. 6b). CYP1A1 is expressed in fetal liver during the first and second trimester and also in other fetal tissues like lung and adrenal tissue and can not be detected anymore in adult liver whereas CYP1A2, CYP2C9 and CYP3A4 expression is absent in fetal liver and expressed in adult liver (Hines et al. 2002).

As outlined above, the first step of the differentiation protocol is the induction of hPSC differentiation towards definitive endoderm (DE). In this protocol a high ratio of differentiation of hPSC into DE cells is achieved by treatment with a high activin A concentration in low serum conditions. Examples of suitable culture media may be based on RPMI Advanced medium. The culture medium may be supplemented one or more of the ingredients Glutamax-I from 0.5 to 2%, bFGF from 1 to 10 ng/ml, Activin A from 10 to 200 ng/ml or Gentamycin from 10 to 200 µg/ml. Alternatively or for use subsequently, another suitable culture medium may be based on RPMI Advanced medium and comprise one or more of the ingredients Glutamax-I from 0.5 to 2%, FCS (Heat-Inactivated) from 0.1 to 1%, bFGF from 1 to 10 ng/ml, Activin A from 10 to 200 ng/ml or Gentamycin from 10 to 200 µg/ml.

This step is crucial for successful further cell differentiation towards liver cells. After DE induction the next two differentiation steps direct differentiation of the cells towards a hepatoblasts phenotype. The final step should support cell maturation into fully differentiated hepatocytes.

To evaluate the applied differentiation conditions the levels of insulin and activin A were analyzed. This analysis revealed an overlap of high levels of insulin with high levels of activin A (FIG. 6a). The observed high level of insulin comes from the serum replacer contained in the culture media (e.g. DM-A) and can support hPSC proliferation and selfrenewal by stimulation of insulin-like growth factor-1 receptor signaling together with ERBB2 receptor signaling. It has also been shown that signaling by activin/nodal family members in combination with reduced insulin/insulin-like growth factor signaling is critical for cell fate commitment into DE. This shows that the differentiation conditions of concurrent high insulin and activin A levels in the bioreactors were not optimal for induction of DE and that this is most likely the reason for absence of hepatic differentiation. Therefore, further experiments were carried out to refine the directed differentiation of hPSC cells to DE and then to a more mature hepatic phenotype, using two Bioreactors run in parallel, BR2 & BR3. This process involved partially differentiating the hPSC towards DE fate first in a conventional 2D flask using high levels of Activin A and other growth factors before inoculating them into bioreactors at a certain time point (process detailed in Example 19 and shown schematically in Tables 4 and 5). This improved process showed higher expression levels of several key hepatic markers in cells inoculated at day 12 into the bioreactor and harvested at day 24 compared to the 2D control; specifically five markers (Albumin, CYP1A2, CYP2C9, CYP7A1 and UGT2B7) all showed significantly higher expression in the bioreactor-cultured samples (FIG. 7). Several transporter genes were also upregulated in the bioreactor cultured cells (FIG. 9), most notably ABCC2/MRP2 and FABP1 although it should be noted that expression of these is not totally restricted to hepatic cell types. Importantly, it was also found that expression of Nanog and Oct4, two markers for undifferentiated cells, was undetectable in bioreactor cultured cells (and in the 2D control) compared to the initial, undifferentiated, starting material (FIG. 10).

Subsequent to this, experiments described above were repeated to ensure that results were reproducible across more than one bioreactor. Cells were cultured as described above and inoculated into one of two bioreactors, either BR121 or BR168 at two different time points (day 7 for BR121 or day 12 for BR168). Cells were matured as described (Example 5) and harvested at day 26 before being processed as described in Examples 8-11. Results from BR168 show that several hepatic markers were significantly upregulated in bioreactor matured cells as compared to 2D controls, including CYP3A7, CYP7A1, CYP3A4, CYP1A2 and TAT (FIGS. 11B and D). Importantly, BR121-grown cells also showed upregulation of hepatic markers when compared to 2D controls, including CYP3A7 and Albumin where a nearly 100-fold increase was observed (FIG. 11A and C). Cells in both Bioreactors also showed a marked downregulation of expression of two markers of undifferentiated cells (Oct4 and NANOG), (FIG. 12), confirming that cells had differentiated and were no longer pluripotent.

Included below is a proposed protocol for hepatic differentiation of hBS cells. Depending on starting material and cell output, steps may be omitted or iterated. A person skilled in the art may substitute the individual ingredients with one or more having the same function, see also Table 6 for details of media used in later Bioreactor runs, such as in BR121 and BR168, which may also be used in part or wholly as basis for differentiation experiments.

The culture media used during the differentiation protocol may comprise the ingredients as listed below, however ingredients may be replaced or concentrations adjusted to optimize the growth media to different protocols.

| hPS culture medium | |
|---|---|
| Base | Knockout DMEM |
| 0.5-2% | Glutamax-I |
| 0.5-2% | NEAA |
| 10-50% | Knockout Serum Replacer |
| 20-75 µg/ml | Gentamycin |
| 0.05-1 mM | β-Mercaptoethanol |
| 1-25 ng/ml | bFGF |

| DM-A | |
|---|---|
| Base | RPMI Advanced medium |
| 0.5-2% | Glutamax-I |
| 1-10 ng/ml | bFGF |
| 10-200 ng/ml | Activin A |
| 10-200 µg/ml | Gentamycin |

| DM-B | |
|---|---|
| Base | RPMI Advanced medium |
| 0.5-2% | Glutamax-I |
| 0.1-1% | FCS (Heat-Inactivated) |
| 1-10 ng/ml | bFGF |
| 10-200 ng/ml | Activin A |
| 10-200 µg/ml | Gentamycin |

| DM-C | |
|---|---|
| Base | RPMI Advanced Medium |
| 0.5-2% | Glutamax-I |
| 10-250 ng/ml | aFGF |
| 1-50 ng/ml | bFGF |
| 10-200 ng/ml | BMP2 |
| 50-500 ng/ml | BMP4 |
| 0.05-1% | FCS (Heat-Inactivated) |
| 10-200 µg/ml | Gentamycin |

| DM-D | |
|---|---|
| Base | Williams E (Phenol red free) |
| 1-2x/500 ml | SingleQuots ® |
| 0.5-2% | Glutamax |
| 0.5-5 g/l | D-Galactose |
| 0.5-5 g/l | D-Sorbitol |
| 5-50 ng/ml | HGF |
| 0.5-5 ng/ml | bFGF |
| 10-200 µg/ml | Gentamycin |

| DM-E | |
|---|---|
| Base | Williams E (Phenol red free) |
| 1-2x/500 ml | SingleQuots |
| 0.5-2% | Glutamax |
| 0.5-5 g/l | D-Galactose |
| 0.5-5 g/l | D-Sorbitol |
| 1-25 ng/ml | Oncostatin M |
| 0.5-10 ng/ml | HGF |
| 0.5-10 ng/ml | bFGF |
| 0.05-2 µM | Dexametasone |
| 10-200 µg/ml | Gentamycin |
| 0.15 to 5 µM | rho kinase inhibitor e.g. BIO |

| IDM-A wherein the cells may be cultured for 0.5 to 10 days, such as e.g 2 days RPMI 1640 (+0.01% to 5% PEST, +0.1 to 10% Glutamax) | |
|---|---|
| 0.5 to 2x | B27 |
| 10 to 200 ng/ml | Activin A |
| 0.1-10 mM | NaB |

| IDM-B, wherein the cells may be cultured for 1 to 10 days, such as e.g 5 days RPMI 1640 (+0.01% to 5% PEST, +0.1 to 10% Glutamax) | |
|---|---|
| 0.5 to 2x | B27 |
| 10 to 200 ng/ml | Activin A |
| 0.1-8 mM | NaB |

| PM-A, wherein the cells may be cultured for 1 to 10 days, such as e.g 3 days RPMI A (+0.01% to 5% PEST, +0.1 to 10% Glutamax) | |
|---|---|
| 10 to 200 ng/ml | aFGF |
| 0.5 to 50 ng/ml | bFGF |
| 5 to 250 ng/ml | BMP2 |

| PM-A, wherein the cells may be cultured for 1 to 10 days, such as e.g 3 days RPMI A (+0.01% to 5% PEST, +0.1 to 10% Glutamax) | |
|---|---|
| 20 to 500 ng/ml | BMP4 |
| 0.02 to 5% | FBS |

| VHM-A, wherein the cells may be cultured for 1 to 10 days, such as e.g 2 days VitroHES | |
|---|---|
| 0.1 to 10% | DMSO |

| VHM-B, wherein the cells may be cultured for 1 to 20 days, such as e.g 7 days VitroHES | |
|---|---|
| 0.2 to 20% | DMSO |

| MM-A, wherein the cells may be cultured for 1 to 30 days such as e.g. 20 days WME + SQ (−GA1000) (+1% Glutamax + 0.1% PEST) | |
|---|---|
| 1 to 100 ng/ml | OsM |
| 0.01 to 15 µM | DexM |
| 2 to 50 ng/ml | HGF |
| 0.1 to 3% | DMSO |
| 0.15 to 5 µM | rho kinase inhibitor e.g. BIO |

(SingleQuots® consist of hEGF, Transferrin, Hydrocortisone, BSA, Ascorbic Acid, Insulin with proprietary concentrations)

ABBREVIATIONS

AA; Activin A
Albumin (ALB)
alpha-fetoprotein (AFP)
Definitive endoderm (DE)
FBS; fetal bovine serum
FGF2; Fibroblast growth factor 2
Fibroblast growth factor (FGF)
Forkhead box A2 (FOXA2)
Hepatocyte nuclear factor 4, alpha (HNF4A)
hPSs; human pluripotent stem cells
Human embryonic stem cells (hESCs)
KO-SR; knockout serum replacement.

DEFINITIONS

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson, J. A. et al. (1998), Heins, N. et. al. (2004), human blastocyst derived stem (hBS) cells as well as induced pluripotent stem cells [see, e.g. Yu, J. et al., (2007); Takahashi, K. et al. (2007)]. The various methods and other embodiments described herein may require or utilise hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein, the term "blastocyst-derived stem cell" is denoted BS cell, and the human form is termed "hBS cells" or "hBSC". In literature the cells are often referred to as embryonic stem cells, and more specifically human embryonic stem cells (hES cells or hESC). The pluripotent stem cells used in the present invention can thus be embryonic stem cells prepared from blastocysts, as described in e.g. WO 03/055992 and WO 2007/042225, or be commercially available hBS cells or cell lines.

As used herein "hiPS cells" or hiPSC" refers to human induced pluripotent stem cells.

Further examples of hPS cells include as examples, human adult germline cells isolated from testis (Conrad et al. 2008; Kossack et al. 2008; Gallicano et al. 2009). These cells exhibit similar characteristics as hESC: They express the pluripotency markers OCT3/4, NANOG, SSEA-4, TRA1-81, and TRA1-60, showed high telomerase activity and could be cultured for more then 40 passages while maintaining a normal karyotype. In vitro they can be differentiated into various types of somatic cells of all three germ layers and form teratomas when transplanted in immunodeficient mice. It has also recently demonstrated that by transduction of stemness factors somatic cells can be reprogrammed into pluripotent cells, so called induced pluripotent stem cells (iPSC). First, the induction of pluripotent capabilities in fibroblasts from mouse tail-tip employing retroviral-mediated transduction of OCT4, SOX2, KLF4 and C-MYC has been shown (Takahashi et al. 2006). Further reports demonstrated that the combined expression of four transcription factors, OCT4, SOX2, NANOG and LIN28 or OCT4, SOX2, KLF4 and C-MYC is sufficient to reprogram human fetal foreskin or adult human dermal fibroblasts into pluripotent cells (Takahashi et al. 2007). These human iPSC resemble human embryonic stem cells by their morphologic and gene expression properties. iPSC have normal karyotypes, express telomerase activity, express cell surface makers and genes that characterize human ES cells, and maintain the developmental potential to differentiate into advanced derivatives of all three primary germ layers, including teratoma formation when transplanted into immunodeficient mice.

As used herein "definitive endoderm (DE)" and definitive endoderm cells (DE-cells) refers to cells exhibiting such as but not limited to protein or gene expression and or/or morphology typical to cells of the definitive endoderm or a composition comprising a significant number of cells resembling the cells of the definitive endoderm.

As used herein, "hepatic progenitors" or "hepatic progenitor cells" refers to refers to cells exhibiting markers such as but not limited to protein or gene expression and/or morphology typical to cells of the definitive endoderm or a composition comprising a significant number of cells resembling the cells of the hepatic progenitors.

As used herein, "hepatocyte-like cells (HCLC)" is intended to mean a cell type which is expressing at least some mature hepatic markers such as Albumin, CYP3A4, UGT2B7, OATP-2, ADH1A, UGT1A6, CYP2C9, CYP2C19 and CYP2D6.

As used herein, the term "tissue-like 3D structure" is intended to mean an in vitro derived 3D (3-dimensional) structure derived from a pluripotent starting material.

As used herein, the term "hepatic tissue-like 3D structure" is intended to mean an in vitro derived tissue resembling hepatic organ like tissue.

As used herein feeder cells are intended to mean supporting cell types used alone or in combination. The cell type may further be of human or other species origin. The tissue from which the feeder cells may be derived include embryonic, fetal, neonatal, juvenile or adult tissue, and it further includes tissue derived from skin, including foreskin, umbilical chord, muscle, lung, epithelium, placenta, fallopian tube, glandula, stroma or breast. The feeder cells may be derived from cell types pertaining to the group consisting of human fibroblasts, fibrocytes, myocytes, keratinocytes, endothelial cells and epithelial cells. Examples of specific cell types that may be used for deriving feeder cells include embryonic fibroblasts, extraembryonic endodermal cells, extraembryonic mesoderm cells, fetal fibroblasts and/or fibrocytes, fetal muscle cells, fetal skin cells, fetal lung cells, fetal endothelial cells, fetal epithelial cells, umbilical chord mesenchymal cells, placental fibroblasts and/or fibrocytes, placental endothelial cells.

As used herein, the term "mEF cells" or "MEF cells" is intended to mean mouse embryonic fibroblasts.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

As used herein the term "ROCK Inhibitor" is intended to mean a small molecule inhibitor of the Rho-kinase, such as Y-27632 or Fasudil.

EXAMPLES

Example 1

Culture of Human Foreskin Fibroblasts (HFF)

HFF were purchased from the Type Culture Collection (CRL-2429; Manassas, Va., USA) and expanded in Iscove's Modified Dulbecco's Medium (IMDM) containing GlutaMax-1 (Invitrogen), 10% fetal calf serum and 10,000 U/10,000 µg/ml penicillin/streptomycin (all Biochrom, Berlin, Germany) for not more than 44 population doublings. The cells were inactivated by gamma irradiation with 3000 rad and plated on 0.1% gelatin (Sigma-Aldrich)-coated culture dishes at a density of 30,000-70,000 HFFs per cm2 in Vitro-HES medium (Vitrolife AB, Göteborg, Sweden) supplemented with 10 ng/ml human recombinant basic fibroblast growth factor (hrbFGF) (PeproTec) or Knockout DMEM containing 20% Knockout SerumReplacer, 2 mM GlutaMax-I (all Invitrogen), 0.1 mM nonessential amino acids (NEAA), 50 µg/ml Gentamycin (all Biochrom), 0.1 mM β-mercaptoethanol (Sigma), 10 ng/ml hrbFGF (PeproTec, London, UK). Irradiated cell that were not directly used were frozen down in aliquots in fetal calf serum (Biochrom) containing 10% dimethyl sulfoxide (DMSO) (Sigma-Aldrich) and stored at −152° C. for later use.

Example 2

Culture of Mouse Embryonic Fibroblasts (MEF)

MEFs were expanded in Dulbecco's modified Eagle's medium (DMEM) containing 10% fetal calf serum, 2 mM L-glutamine, 0.1 mM NEAA and 10,000 U/10,000 µg/ml penicillin/streptomycin (all Biochrom) for 2 to a maximum of 4 passages. Inactivated by gamma irradiation with 3000 rad and seeded to 0.1% gelatin (Sigma-Aldrich) coated "In Vitro Fertilization" (IVF) dishes (Falcon, Becton Dickinson) at a density of 65,000 cell/cm2 in VitroHES medium (Vitrolife AB) or frozen down in aliquots in fetal calf serum (Biochrom) containing 10% DMSO (Sigma-Aldrich) and stored at −152° C. for later use.

Example 3

The Bioreactor

The multi-compartment bioreactors used for the studies are composed of three independent, yet interwoven hollow fiber capillary membrane systems that are integrated into a two-component polyurethane housing (PUR, Morton, Bremen, Germany). Two hydrophilic capillary systems for medium perfusion are made of microporous polyethersulfone capillary membranes with a molecular weight cut-off of approximately MW 500,000 (mPES, Membrana, Wuppertal, Germany). The third one is made of hydrophobic multilaminate hollow fiber membrane capillaries (MHF, Mitsubishi, Tokyo, Japan) to enable gas exchange. The cells located within the extra-capillary space are thus exposed to decentralized medium supply with high mass exchange rates and direct membrane oxygenation via diffusion. For cell injection, a flow head and open ending silicone rubber capillaries (Silastic, Dow Corning, N.Y., USA) are used (FIG. 1A, B and C). The bioreactor is integrated into a processor controlled perfusion device with pressure- and flow regulation for modular pumps with exchangeable multichannel flowheads and gears for medium recirculation and substitution (FIG. 2 A and C). A heating unit provides a constant temperature within the perfusion circuit. Flow rates of air and $CO_2$ were either manually controlled using integrated rotameters or by using an external automated $CO_2$-regulated pH control system (FIG. 2). The control device continuously measures the pH value of the culture medium via an optical pH sensor integrated into the bioreactor perfusion circuit and adjusts the air/$CO_2$ mixture to maintain a preset pH. Perfusion tubings with bubble traps (shown in FIG. 2C) were made from standard medical grade dialysis PVC (B. Braun, Melsungen, Germany). Sterilization was performed with ethylene oxide or formaldehyde gas followed by a degassing period of at least 7 days. During the experiment perfusion devices were connected via an integrated USB port to a PC and the perfusion parameters (pressure, temperature, pump speeds) were continually recorded and graphically monitored using a stand alone measurement program created with LabVIEW (National Instruments, Munich, Germany). The program also provides a web server that enables remote monitoring via the internet (FIG. 2C).

Example 4

Bioreactor Conditioning

Before initial cell inoculation bioreactors underwent a conditioning phase of 24-72 hours with recirculation of medium. After cell inoculation cultures were perfused at a flow rate of 22-30 ml/minute. The bioreactors were kept at 37° C. The flow of the air/$CO_2$ mixture in the gas compartment was maintained at 40 ml/minute. The pH, partial pressures of oxygen ($pO_2$) and carbon dioxide ($pCO_2$) and the acid/base status were periodically measured (ABL 5, Radio Meter Copenhagen, Copenhagen, Denmark). In case of manual gas control the air/$CO_2$ mixing ratio was adjusted to maintain a stable pH between 7.2 and 7.3. To allow online storage, access and analysis of the metabolic and perfusion data generated throughout the experiments a database was developed.

Example 5

Hepatic Differentiation of hESC in the Bioreactor-HepDiff-1 and HepDiff-2

Two initial bioreactor runs were performed to examine directed hepatic differentiation. In one experiment the bioreactor was seeded with inactivated MEF two days before hESC inoculation while the other one was conducted without feeder cell addition (see Table 1 and Table 2). To induce hepatic differentiation of the hESC, bioreactors were perfused successively with five different media (DiffMed1-5, Table 2) based on a differentiation protocol developed by Applicant. An overview of the sequence, composition and fresh medium addition rates to the perfusion circuit of the media is shown in Table 2.

Example 6

Metabolic Parameters in the Perfusion Medium

The metabolic activity and differentiation of the cells inside the bioreactors were characterized on a daily basis by measuring soluble factors in the medium outflow and in the recirculating medium. The following parameters were measured using automated clinical chemistry analyzers (Roche Diagnostics, Heidelberg, Germany): α-fetoprotein (AFP), alkaline phosphatase (AP), alanine transaminase (ALT), aspartate transaminase (AST), beta-human chorionic gonadotropin (β-hCG), c-peptide, carcinoembryonic antigen (CEA), cytokeratin fragment 19 (Cyfra 21-1), erythropoetin, estradiol, follicle stimulating hormone (FSH), factors II-V-X-XIII, fibrinogen, gamma-glutamyltransferase (GGT), glucose, lactate, lactate dehydrogenase (LDH), luteinizing hormone, neuronspecific enolase (NSE), osmolality, osteocalcin, pseudocholinesterase (PCHE), prealbumin progesterone, prolactin, S-100, thyroid-stimulating hormone (TSH), tissue plasminogen activator (TPA), transferrin (for a detailed description of the measurement methods see Table 8 in appendix). Additionally glutamine, glutamate, glucose, lactate, ammonium, pH, sodium (Na+), potassium (K+) were measured with a BioProfile 100 Plus device (Nova Biomedical, Waltham, Mass., USA). Activin A, insulin and albumin were measured with enzyme-linked immunosorbent assays (ELISAs) following the manufacturer's recommendations (activin A using products DY338, DY999, DY994, DY995 from R&D Systems, Wiesbaden-Nordenstadt, Germany; insulin using an ELISA from Invitrogen; albumin using an ELISA from Albuwell, Exocell Inc., Philadelphia, Pa., USA). Urea was measured using a colorimetric determination kit (QuantiChrom, BioAssay Systems, Hayward, Calif., USA). Galactose and sorbitol concentrations were measured by enzymatic assays (Roche Diagnostics).

The production or consumption rate of each substance was calculated per bioreactor per day by multiplying the actual waste volume of the day by the difference between the substance concentration in the feed medium and that in the waste medium.

Example 7

Metabolic Activity

Bioreactor cultures that were treated with the hepatic differentiation protocol were tested or their ability to metabolize phenacetin, diclofenac and midazolam via the phase I cytochrome (CYP) P450 enzymes CYP1A2, CYP2C9 and CYP3A4, respectively. At days 40 and 47 after inoculation of the cells a CYP P450 activity test was performed according to the scheme:

| CYP1A2: | Phenacetin –> | Acetaminophen |
|---|---|---|
| CYP2C9: | Diclofenac –> | 4'OH diclofenac |
| CYP3A4: | Midazolam –> | 1'OH midazolam |

For this purpose, fresh medium inflow and medium outflow was closed and a cocktail of the test substances was injected into the recirculating medium to get the following concentrations at the beginning of the test: 3 µM Midazolam, 9 µM Diclophenac and 26 µM Phenacetin. During the next 24 hours, the bioreactor was operated in recirculation mode (no fresh medium was added and only the medium recirculation pump recirculates the medium). Samples from the recirculation were taken before starting the experiment and after 1, 4, 8 and 24 hours and analyzed for the metabolites of the test substances by liquid chromatography/mass spectrometry (LC/MS). Analyses were performed at Astrazeneca AB, Gothenburg, Sweden. After the last sample was taken the bioreactor was flushed with fresh medium in single pass mode with two times the volume of the bioreactor and tubing system and then switched to the normal perfusion mode recirculation with fresh medium inflow).

Example 8

Sample Acquisition from the Bioreactor

At the end of the scheduled culture period, bioreactors were shut down and the tubing was disconnected. The lower bioreactor lid was opened and samples of the cell mass including the capillary layers were cut out using sterile scalpels and forceps for further analysis. For histological analysis samples were directly fixed and embedded as described below. For teratoma testing, FACS and RNA analysis, cells were separated from the capillaries and dissociated by washing with PBS w/o CaMg and incubation for 3 minutes in 0.05%-0.02% trypsin-EDTA solution (Biochrom). Trypsination was stopped by addition of DMEM containing 10% fetal calf serum (Biochrom). Separation of the capillaries from the cell solution was achieved by sieving using a 100 µm cell strainer (Falcon, Becton Dickinson, Heidelberg)

Example 9

Isolation of RNA

To isolate RNA from cells/tissue cultured in the bioreactor excised capillaries were washed with PBS w/o CaMg and incubated for 3 min in 0.05%-0.02 trypsin-EDTA solution (Biochrom). Total RNA was isolated using the RNeasy Kit (Qiagen, Hilden, Germany) following the manufacturer's protocol. Teratomas were disrupted using a TissueLyser II followed by homogenization with a QIAshredder (both Qiagen). Single cells were lysed by direct addition of lysis buffer to the cell pellet. The concentration and quality of the isolated RNA was determined using a Nanodrop spectrophotometer (Thermo Fischer Scientific) and with a Bioanalyser (Agilent 2100 Bioanalyser) or by native agarose gel electrophoreses.

Example 10

Array Hybridisations

Biotin-labeled cRNA was generated using the Illumina® TotalPrep RNA Amplification Kit (Ambion, Austin, Tex., USA) with 300 ng of quality-checked total RNA as input. Chip hybridizations, washing, Cy3-streptavidin (Amersham Biosciences) staining, and scanning were performed on an Bead Station 500 (Illumina, San Diego, USA) platform using reagents and following protocols supplied by the manufacturer. cRNA samples were hybridized on Illumina human-8v2 BeadChips, which harbor approximately 24,000 RefSeq transcripts (Kuhn et al. 2004).

Example 11

Data Analysis

Quantil normalized and non-normalized RAW data files for all samples were generated using the BeadStudio V3 software (Illumina). Further data analysis was performed by importing the data generated with the BeadStudio software into the microarray data analysis tools MultiExperiment Viewer (MeV), a component of the TM4suite (Saeed et al. 2003) or Chipster, which is a graphical interface that uses Bioconductor (Gentleman et al. 2004) as its analysis backend. Functional enrichment analysis was performed using DAVID (Dennis et al. 2003).

Example 12

Histochemistry

Paraffin embedded samples were fixed in 4% buffered formaldehyde solution, embedded in paraffin and cut into 5 µm sections. Sections were deparaffinized with xylene and rehydrated with decreasing alcohol series followed by hematoxylin and eosin (H&E) staining.

Example 13

Immunohistology

Paraffin embedded samples were fixed in 4% buffered formaldehyde solution, embedded in paraffin and cut into 5 µm sections. Sections were deparaffinized with xylene and rehydrated with decreasing alcohol series. Antigens were retrieved by boiling sections for 25 min in a pressure cooker in citrate buffer (0.01 citric acid monohydrate, pH to 6.0; Merck, Darmstadt, Germany) followed by incubation for 20 min in 5% Triton/PBS. Sections were blocked with 5% skim milk; they were incubated with primary antibodies for 30 min, washed with PBS and incubated with the secondary fluorescence conjugated antibodies. The following primary antibodies were used: monoclonal mouse anti human smooth muscle actin IgG2a (ASMA), monoclonal mouse anti human desmin IgG1 (Dako, Glostrup, Denmark), monoclonal mouse anti neuron-specific β-III-Tubulin IgG2a (R&D Systems), monoclonal mouse anti nestin IgG1 (Becton Dickinson), polyclonal goat anti HNF-3β IgG, monoclonal mouse anti OCT-4 IgG2b and polyclonal rabbit anti vimentin IgG (Santa Cruz Biotechnology). As secondary antibodies the following polyclonal antibodies were used: goat anti mouse IgG-Cy2, goat anti rabbit IgG-Cy3 (Dianova), goat anti mouse IgG2a-TRICT, goat anti mouse IgG-FITC, goat anti mouse IgG-FITC, goat anti mouse IgG-Cy3, goat anti mouse IgG-FITC (Jackson Immunoresearch Laboratories, West Grove, Pa.) and donkey anti goat IgG-Cy3 (Santa Cruz Biotechnology). For non-specific staining of the nuclei, sections were incubated with 4',6-diamidino-2-phenylindole (DAPI, Molecular Probes, Leiden, Germany).

Subsequently the sections were mounted with Aqua Polymount solution (Polysciences Inc., Warrington, Pa., USA. Sections were analyzed using an inverse microscope (Axiovert 200M, Carl Zeiss, Gottingen, Germany) equipped with a CCD-camera (Retiga 2000R, QImaging, Burnaby, Canada). The pictures were acquired and processed using the digital imaging software "Image Pro Plus" (Media Cybernetics, Silver Spring, USA).

Example 14

Transmission Electron Microscopy (TEM)

Material from the bioreactor cell compartment was fixed with 5% glutaraldehyde (Serva, Heidelberg, Germany). After immersion for 30 minutes in 60 mmol/l phosphate buffer, pH 7.3, the cellular aggregates were post-fixed in 2% OsO4 (Paesel+Lorei, Frankfurt, Germany) for 2 h, progressively dehydrated in ethanol and then embedded in araldite (Serva, Heidelberg, Germany). Ultra-thin sections were contrasted with uranyl acetate and Reynold's lead citrate (Chroma, Munster, Germany) before electron microscopic examination.

Example 15

Improved Hepatic Differentiation of hESC in the Bioreactor

Based on the results from the initial hepatic differentiation runs as described in example 5 additional runs were performed to further examine directed hepatic differentiation.

In one experiment feeder free cultured hESC was differentiated into DE in 2D culture outside the bioreactor according to the differentiation protocol as described herein. This first differentiation step into DE towards hepatocytes induces a lot of cell death. By doing this step outside the bioreactors, major cell debris in the reactors are avoided. Additionally, carrying out the first differentiation step in 2D allows a more pure selection of definitive endoderm cells, leading to overall more pure cultures with significant amounts of definitive endodermal cells in the cultures.

After differentiation into DE, the cells were transferred to to the bioreactors, or as a control, kept in 2D. To induce further hepatic differentiation of the definitive endoderm cells, bioreactors were perfused successively with different medias based on differentiation protocols developed by Cellartis. An overview of an example of the sequence, composition and fresh medium addition rates to the perfusion circuit of the media is shown in Table 2.

Example 16

Production of Conditioned Medium with the Bioreactor System for Culture of Undifferentiated hESC The bioreactor experiments as discussed herein also show that the presence of inactive HFF delays the start of hESC differentiation until the HFF loose their activity. The pluripotency supporting activity of the HFF could be correlated with their production of activin A. To further examine the behaviour of the HFF feeder cells several experiments only with HFF were carried out in 2D cultures and in two bioreactors.

In one experiment, the bioreactor is inoculated with active HFF that will be cultured in medium supplemented with serum and bFGF to stimulate HFF proliferation. Increase of the cell number is monitored by the levels of glucose consumption and lactate production. When a sufficient cell number is reached culture medium is changed to hBS medium for conditioning. Optimal medium exchange rates have to be determined for example measuring activin A and glucose concentrations in the conditioned medium as quality control parameters. A low glucose level might indicate the demand for increasing the medium feed rate and a low activin A level might be a sign for insufficient conditioning unsuitable to promote hESC pluripotency.

Results from 2D and 3D experiments show that activin A production is stimulated by bFGF in combination with medium containing serum replacer. In medium supplemented with serum, bFGF did not stimulate activin A production but exhibited a strong mitogenic effect on active HFF. This effect was also observed in bioreactor experiment HFF-1 characterized by increasing levels of glucose and lactate metabolism upon bFGF addition to the medium. This mitogenic effect was not observed in the bioreactor experiment HFF-2, in which medium supplemented with serum replacement was used. In this experiment glucose and lactate metabolism stayed on a constant level which shows that the cells did not proliferate. These results show that a possible application of the bioreactor technology could be the production of conditioned medium that is needed for feeder free expansion of undifferentiated hESC.

The standard method for the production of conditioned medium (CM) is incubation of culture medium for 24 hours in standard culture vessels seeded with inactive MEF feeder cells at a high density. This method is labour intensive and space consuming, because large numbers of feeder cells have to be produced that can only be used for a limited amount of time for medium conditioning until they loose their activity. Therefore the production of larger volumes of CM is limited by the poor scalability of this method. An alternative approach to the use of CM for culture hBS cells is the use of defined culture media. Several defined medium formulations have been described for feeder independent culture of hESC (Li et al. 2005; Ludwig et al. 2006). While the use of defined medium has several advantages like the possibility to culture hBS cells under conditions completely free of animal derived substances, its major disadvantage is that these media formulations include significant amounts of expensive supplements like recombinant cytokines and growth factors.

Cultivation of HFF in a bioreactor to produce CM could be an alternative to the currently available methods reviewed above in the background section.

It would enable high cell densities of human feeder cells in a scalable system that allows automatic control of the culture parameters and defined rates of medium in and outflow. Therefore standardization of the conditioning process will be possible resulting in an increased quality of the produced CM compared to manual methods. One further advantage when using the bioreactor could be the possibility to use active feeder cells because it has been shown that active feeder cells also support maintenance of pluripotency (Xie et al. 2005). This would decrease the number of active feeder cells that have to be produced in conventional 2D cultures for initial bioreactor inoculation.

Example 17

Assessment of Hepatic Maturation

The degree of maturation of the derived hepatic cells was analysed by measurements of the gene expression, protein expression and as well activity measurements of the Cytochrome P450 (CYP) activity.

Gene Expression Analysis of the Hepatocyte-Like Cells by Q-PCR and LDA Cards

Samples of hepatocyte-like cells differentiated in the bioreactors and adequate controls (either 2D differentiated hepatocyte-like cells or primary hepatocytes from adult human liver) were analysed by QPCR for the expression of hepatic-related genes.

Gene expression of DE-Hep cells was characterised on LDA microfluidity cards as listed in Table below. cDNA derived from total RNA of the samples was hybridised with a LDA card and the experiment ran in a PCR setup and further analysed using suitable software. All samples were run in parallel with adequate controls in repeated experiments on the LDA card following the instructor's manual (Applied Biosystems 7900HT Micro Fluidic Card Getting Started Guide) and the following shortened protocol:

cDNA was prepared from total RNA and diluted it in RNase/DNase-free water to receive a suitable concentration (see below). The following components were mixed: cDNA (1-100 ng), 5 µl, RNase/DNase-free water, TaqMan Universal PCR, 45 µl, Master mix (2×), 50 µl, Total: 100 µl. The samples were thereafter loaded onto the LDA card (each sample mix is 100 ul and 170 ng cDNA per sample) and centrifuged, whereafter the LDA card was sealed. Finally, the card was run on ABI 7900HT real-time PCR system according to the instructions in the manual and the results analyzed by using SDS 2.2.1 software and the relative quantification method.

Example 18

Hepatic Differentiation

Based on a hepatic differentiation protocol established by Cellartis for hESC cultured in 2D standard culture dishes, two pilot experiments on the directed hepatic differentiation of hESC in the 3D bioreactor system were designed and performed. The two bioreactor experiments differed only in the additional inoculation of inactivated MEF into one of the bioreactors.

Metabolic Parameters in the Perfusion Medium

The comparison of the two bioreactors regarding the metabolic parameters measured in the medium shows that the bioreactor, in which additional feeder cells were inoculated (HepDiff-2) initially had a much higher cell activity in terms of glucose and lactate metabolism and regarding the production of differentiation markers. However, in bioreactor HepDiff-2 a steady decrease of glucose consumption and lactate production during the experiment was observed (FIG. 4). The peak of LDH on day 20 was presumably due to technical malfunction of the heating unit of the perfusion system. The peaks of LDH release after day 40 were presumably related to a pressure build up in the bioreactor. Since a precipitation of unidentified medium components was observed, which could lead to clotting of the capillary membranes this might have resulted in suboptimal supply of the cells with nutrients. AFP production in this bioreactor increased exponentially between day 17 and 24 and then decreased until the end of the experiment. The beginning of the down-regulation of AFP production correlates with the change to another differentiation medium. The hepatic differentiation marker urea showed a small peak in its production between day 1 and 20 and albumin production stayed on a relative low level of about 0.4 µg/h during the whole experiment (FIG. 5).

In Bioreactor HepDiff-1, in which no additional MEF were inoculated, very low but stable glucose consumption and lactate production levels were measured. Only the differentiation factor AFP showed a small peak between days 17-35 with a maximum at day 26, which resembles the time course but not the magnitude of AFP in bioreactor HepDiff-2 (FIG. 5).

In addition to the factors described above, the concentrations of activin A and insulin were measured in the culture medium to evaluate the used perfusion conditions with regard to the resulting exchange dynamics of the differentiation media (FIG. 6). Both factors play an important role in inducing differentiation towards definitive endoderm in undifferentiated hESC whereas insulin antagonises endoderm induction through high activin A concentrations. In both bioreactors activin A concentrations in the medium had a maximum of 26 ng/ml between day seven and eight. Insulin concentrations, only measured in bioreactor HepDiff-2 on days 0 to 22, showed a maximum of 150 ng/ml at day 3 and decreased rapidly to 2 ng/ml until day 9 with an intermediate concentration of about 35 ng/ml between day seven and eight.

CYP450 Activity

To test for hepatocyte specific cell activity in the bioreactors the ability to metabolize phenacetin, diclophenac and midazolam via the phase I cytochrome P450 enzymes CYP1A2/1A2, CYP2C9 and CYP3A4, respectively was tested.

The tests were performed at days 40 and 47 after hESC inoculation. In both bioreactors no metabolism of diclophenac and midazolam could be detected. Metabolism of phenacetin into paracetamol was higher in bioreactor HepDiff-2 compared to reactor HepDiff-1 and dropped only slightly on day 47.

Histology

As described above, both bioreactors exhibited a very low metabolic activity at the end of the experiment. This observation correlated with the fact that during histological analysis in bioreactor HepDiff-2 only very few areas containing tissue structures and in the samples of bioreactor HepDiff-1 no structures at all could be found. In the tissue clusters observed in bioreactor HepDiff-2 many structures with different epithelial morphologies could be observed, indicating a pronounced endodermal differentiation. In addition areas with loose connective tissue and a few cell aggregates comprised of cells with a low cytoplasm to nucleus ratio were found.

Example 19

Differentiation of hESC into Hepatocytes and Maturation in Bioreactor

First round of Bioreactors Run in Parallel: BR2 & BR3

Further to the protocols detailed in Example 18, several further experiments were run to refine the procedure for directed differentiation of hESCs to hepatocytes in a bioreactor environment, focusing also on the improved maturation of these cell types. These experiments are detailed in Tables 3 and 4 (Bioreactors BR2 & BR3) which describe the overall procedure for initiating differentiation of hESCs to DE cells using Activin A and high growth factor levels, inoculating the cells into the bioreactor at a given time point (day 12 for experiment shown in Table 3, days 7 or 11 for experiment shown in Table 4) and allowing further differentiation and maturation to occur. This procedure is run in parallel with a 2D non-bioreactor control and for both experiments levels of CYP450 were measured at specified time points prior to bioreactor shutdown at day 25 or 26.

During the initial experimental runs, expression of four groups of markers was measured (Hepatic genes, markers for fetal/immature hepatocytes, transporters and markers for undifferentiated cells.), with measurement time points consisting of Day 0, Innoculation day, and bioreactor shutdown day for cells growing in bioreactor environment, and parallel shutdown day measurements for the 2D control group (shown in FIGS. 7-10 for cells inoculated on day 12 and harvested on day 24). Gene expression levels were measured as described in Examples 9-11 and 17

Second Round of Bioreactors Run in Parallel: BR121 & BR168

Subsequently, results were compared for two separate Bioreactors to ensure consistency and reproducibility. Cells were inoculated into either Bioreactot BR121 or B168 at two different time points (day 7 and day 12) and allowed to mature as follows until day 26 (FIG. 11, A-D):

On day 0, at start of experiment, 200×10$^6$ undifferentiated human embryonic stem cells DEF SA121 was tryple selected for passaging and seeded on matrigel coated culture flasks at 200000 cells pr cm2 in ID1 supplemented with 10 uM Rock Inhibitor. Medium change every day or every second day till day 7 according to the schedule above. After induction of endoderm, on day 7 all cells were tryple selected and counted, 60 million cells total. 30 million cells were used for BR121, 30 millions for BR168.

BR121:

On day 7, 25 million cells were inoculated into BR121 in P1 supplemented with 10 uM Rock Inhibitor and cultured according to schedule above till end of experiment day 26.

million cells were seeded in matrigel coated 48 wells for 2D controls, 150000 cells pr cm2 in P1 supplemented with 10 uM Rock Inhibitor and cultured according to schedule above till end of experiment, day 26.

BR168:

On day 7, 30 million cells were seeded in 2D culture flasks in P1 supplemented with 10 uM Rock Inhibitor and cultured according to schedule above. 5 days later, on day 12, cells were tryple selected and counted, 72 million cells total.

62 million cells were inoculated in BR168 in VH2 supplemented with 10 uM Rock Inhibitor and cultured according to schedule above till end of experiment, day 26.

7 million cells were seeded in matrigel coated 48 wells for 2D controls, 200000 cells pr cm2 in VH2 supplemented with 10 uM Rock Inhibitor and cultured according to schedule above till end of experiment, day 26.

Markers analysed were all hepatic markers and levels were compared to 2D controls. Culture media compositions are described in Table 6.

Example 20

A further aspect of the dynamic perfusion technique is that a combination of "twin bioreactors" in one perfusion circuit can be easily performed, where factors or soluble mediators of a first bioreactor can stimulate the second bioreactor, while cells remain compartmentalized. This would be of interest if unknown soluble factors of a co-culture are to be used, but cell transfer between the cultures has to be avoided.

BRIEF DESCRIPTION OF THE DRAWINGS

Table 1. Table 1 lists the performed experiments Hepdiff 1 and Hepdiff 2 and their experimental conditions.

Table 2. Overview of the sequence and composition of the media used to induce hepatic differentiation of hESC in the bioreactor Table 3. Maturation of hESC to hepatocytes in Bioreactor BR1; Jellyfish 2 ml bioreactor, Flow 2 ml/h=50 ml/day/BR=100 ml pr day. Cells: SA121 DEF, Innoculation at progenitor stage 12. Pink phase: induction of DE (Definitive endoderm), Green phase: Progenitor stage (small hepatocyte-like cells), Blue phase: Maturation Table 4. Maturation of hESC to hepatocytes in Bioreactors BR2 & BR3; Jellyfish 2 ml bioreactor, Flow 2 ml/h=50 ml/day/BR=100 ml pr day. Cells: SA121 DEF, Innoculation at Day 7 (DE stage) and progenitor stage (day 12). Pink phase: induction of DE (Definitive endoderm), Green phase: Progenitor stage (small hepatocyte-like cells), Blue phase: Maturation Table 5. Maturation of hESC to hepatocytes in Bioreactors BR121 & BR168; Jellyfish 2 ml bioreactor, Flow 2 ml/h=50 ml/day/BR=100 ml pr day. Cells: SA121 DEF, Innoculation at progenitor stage 12. Pink phase: induction of DE (Definitive endoderm), Green phase: Progenitor stage (small hepatocyte-like cells), Blue phase: Maturation Table 6. Schematic representation of the culture media and incubation times used in example 19.

REFERENCES

Figure 1:
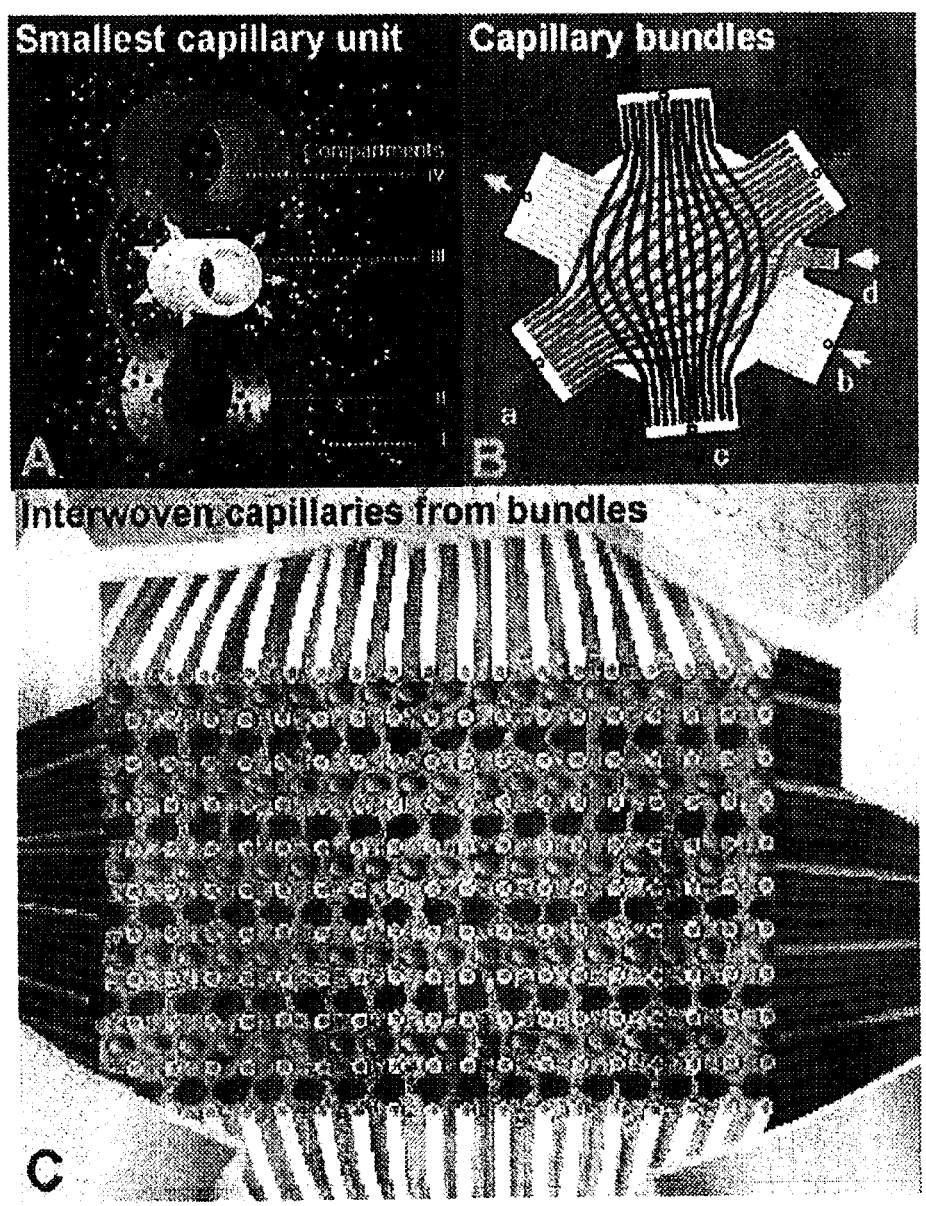
FIGS. 1A-1C. Bioreactor design. A) Smallest capillary membrane unit with independent compartments for medium perfusion (blue, II; red, IV), oxygenation (yellow, III) and cell accommodation (I); B) Capillary membrane bundles constituting these compartments; C) 3D arrangement of the capillaries/compartments within the cell compartment; The compartments can be perfused separately as shown in B, addressing the reduction of substance gradient distances between the capillary units and enhancing mass exchange. All membrane compartments are interwoven with each other within the cell compartment, forming a tight capillary network with intercapillary distances of averagely 500 μm (C). The capillaries of each compartment are bundled to in- and outflow heads, respectively, to be connected to tube systems for perfusion (B). Cells are inoculated into the cell compartment via open ending tubes, which allows distribution of the injected cells within the cell compartment (B, d; shown in grey color).
Figure 2:
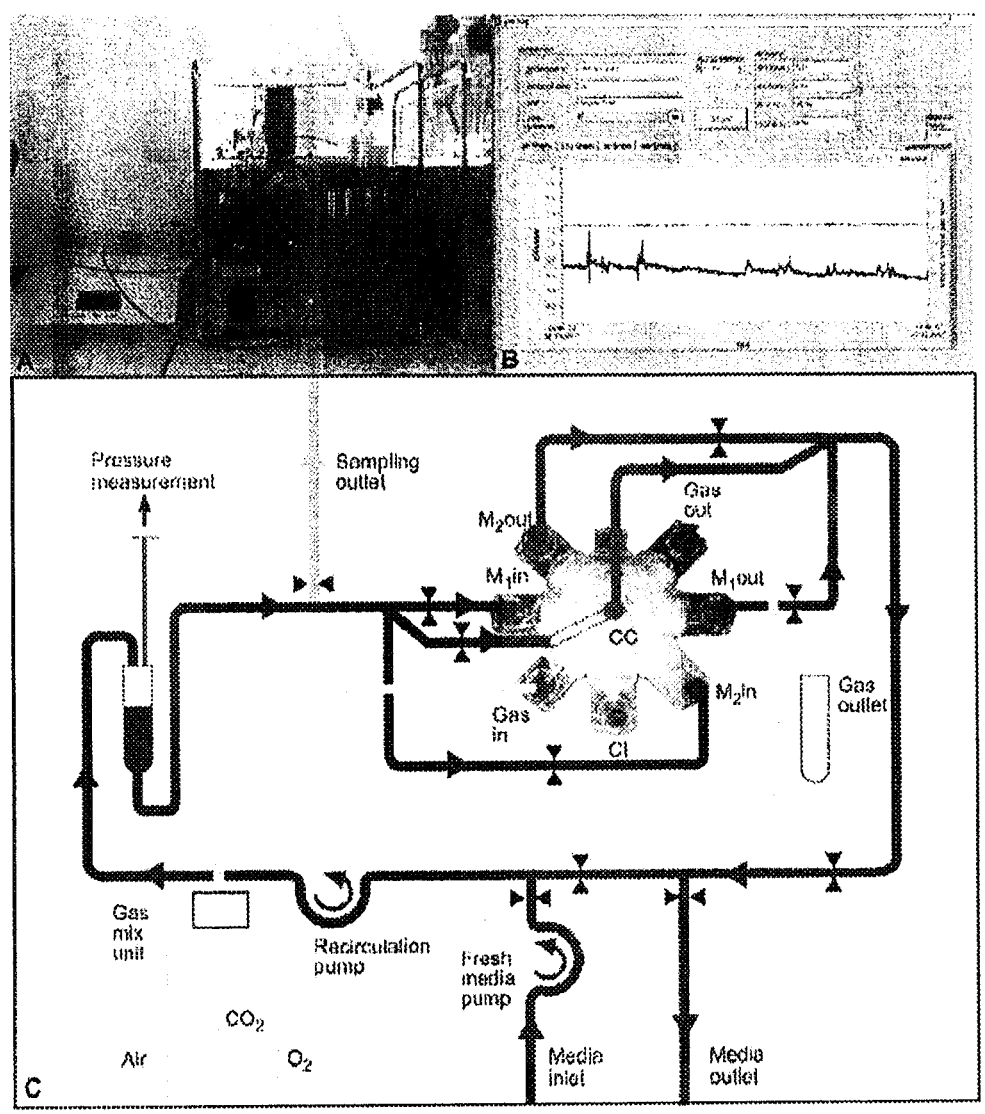
FIGS. 2A-2C. Perfusion system. A) Processor controlled perfusion device with pressure- and flow regulation for modular pumps with exchangeable multichannel flowheads and gears for medium recirculation and substitution and external automated CO2-regulated pH control system (on the left) B) Custom monitoring software that continually records and graphically monitors pressures, temperature, pump speeds, pH and gas flow. C) Schema of the tubing system used to perfuse the bioreactor with medium and gas.
Figure 3:
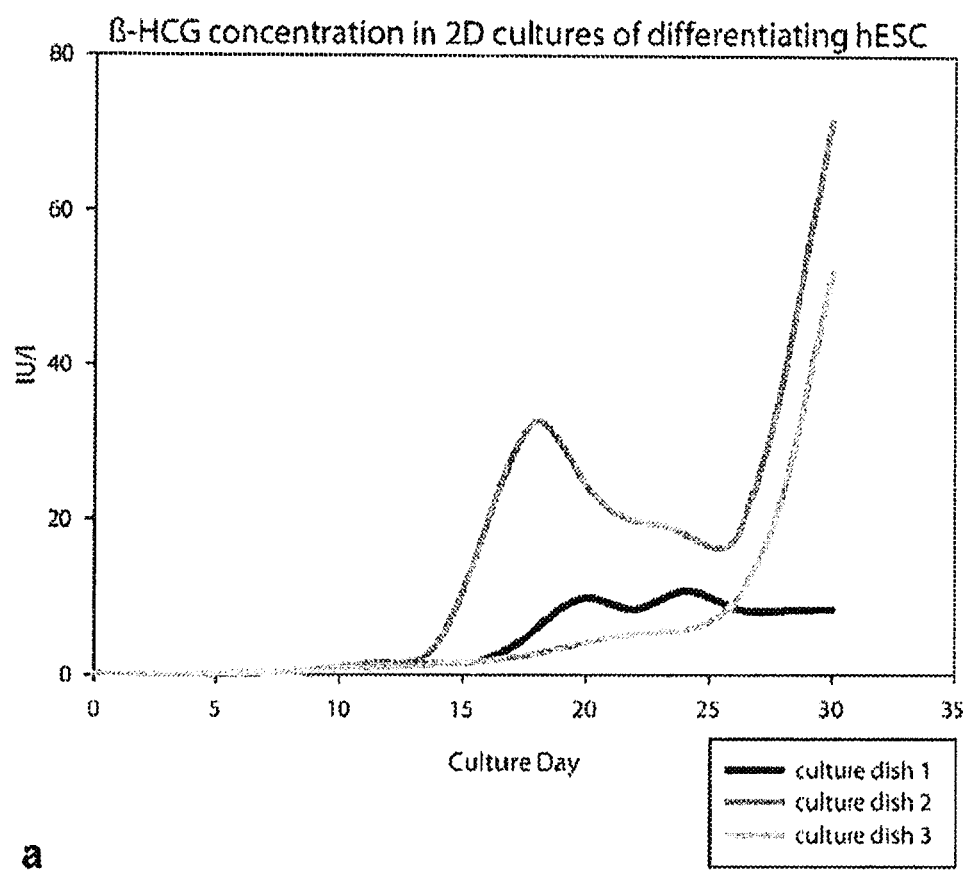
FIG. 3a. β-HGC concentration in 2D culture of differentiated hESC, shown in three separate culture dishes. Culture dish 1 is represented by the curve which is lowest at culture day 30, Culture dish 2 is represented by the curve which is in the middle at culture day 30, Culture dish 3 is represented by the curve which is highest at culture day 30.
Figure 4:
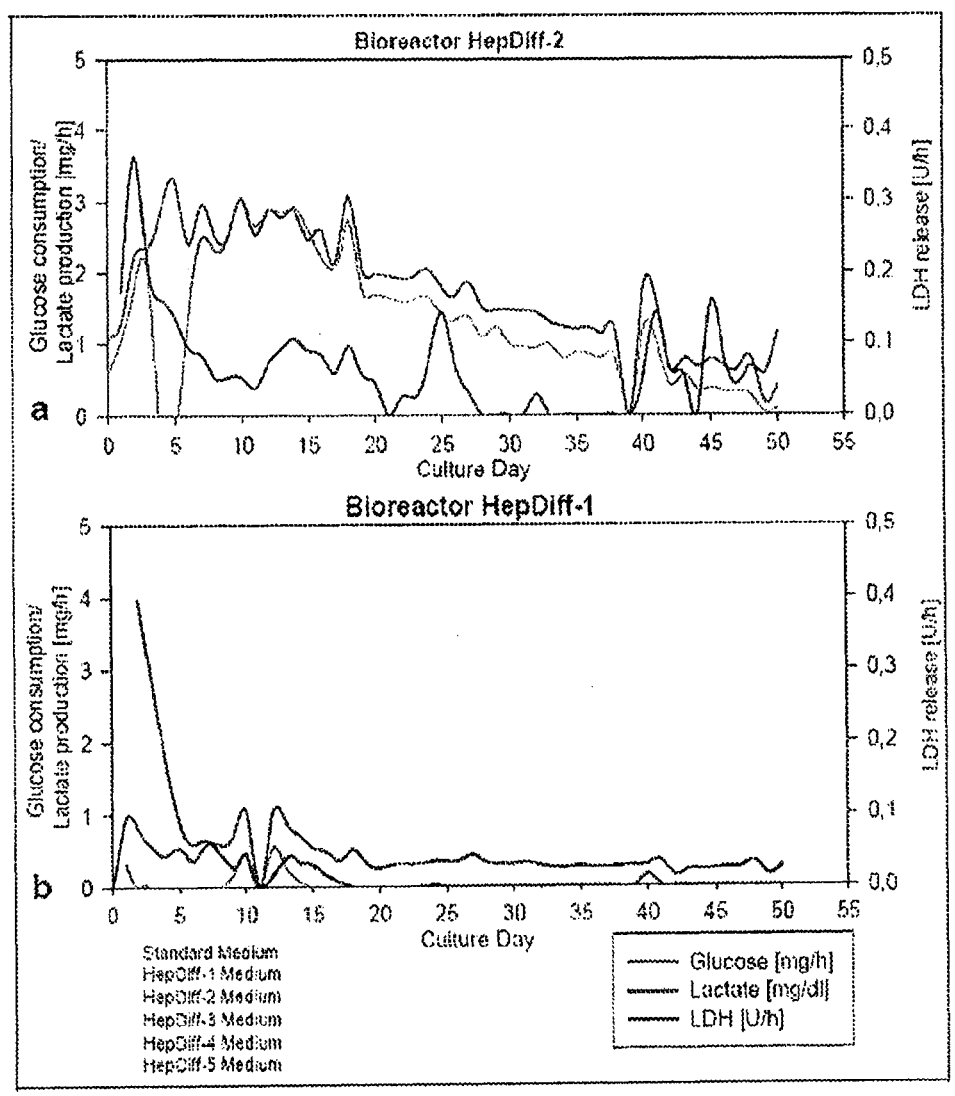
FIGS. 4a-4b. Time course of the metabolic parameters measured in the medium outflow of bioreactors hESC-1, -2 and -3. Glucose consumption (green, lowest curve at start of measurement), lactate production (red, curve in the middle at start of measurement) and LHD release (blue, highest curve at start of measurement) by the cells in bioreactors HepDiff-2 (a) and HepDiff-1 (b).
Figure 5:
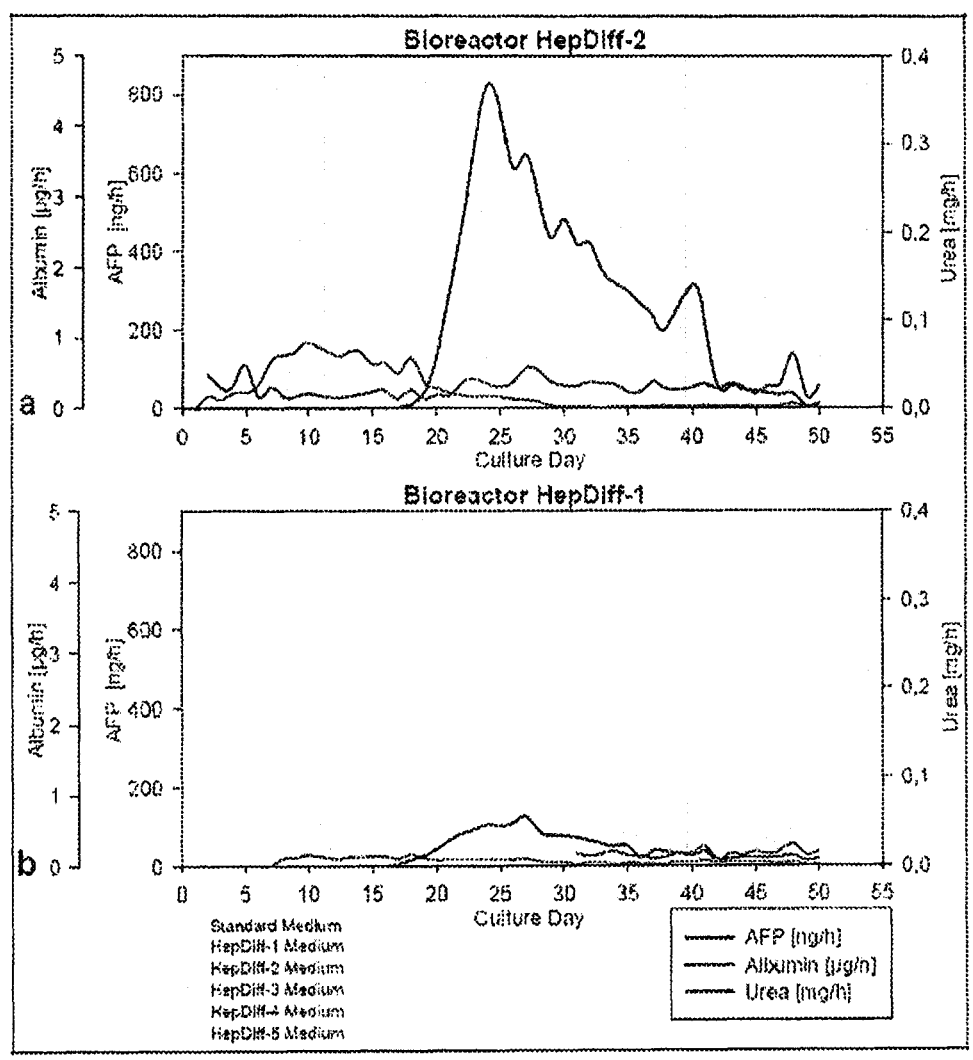
FIGS. 5a-5b. Time course of the differentiation markers measured in the medium outflow of bioreactors HepDiff-1 and -2. AFP production (dark blue, in the middle at day 50), albumin production (dark green, highest curve at day 50), and urea production (pink, lowest curve at day 50) by the cells in bioreactors HepDiff-1 (a) and HepDiff-2 (b).
Figure 6:
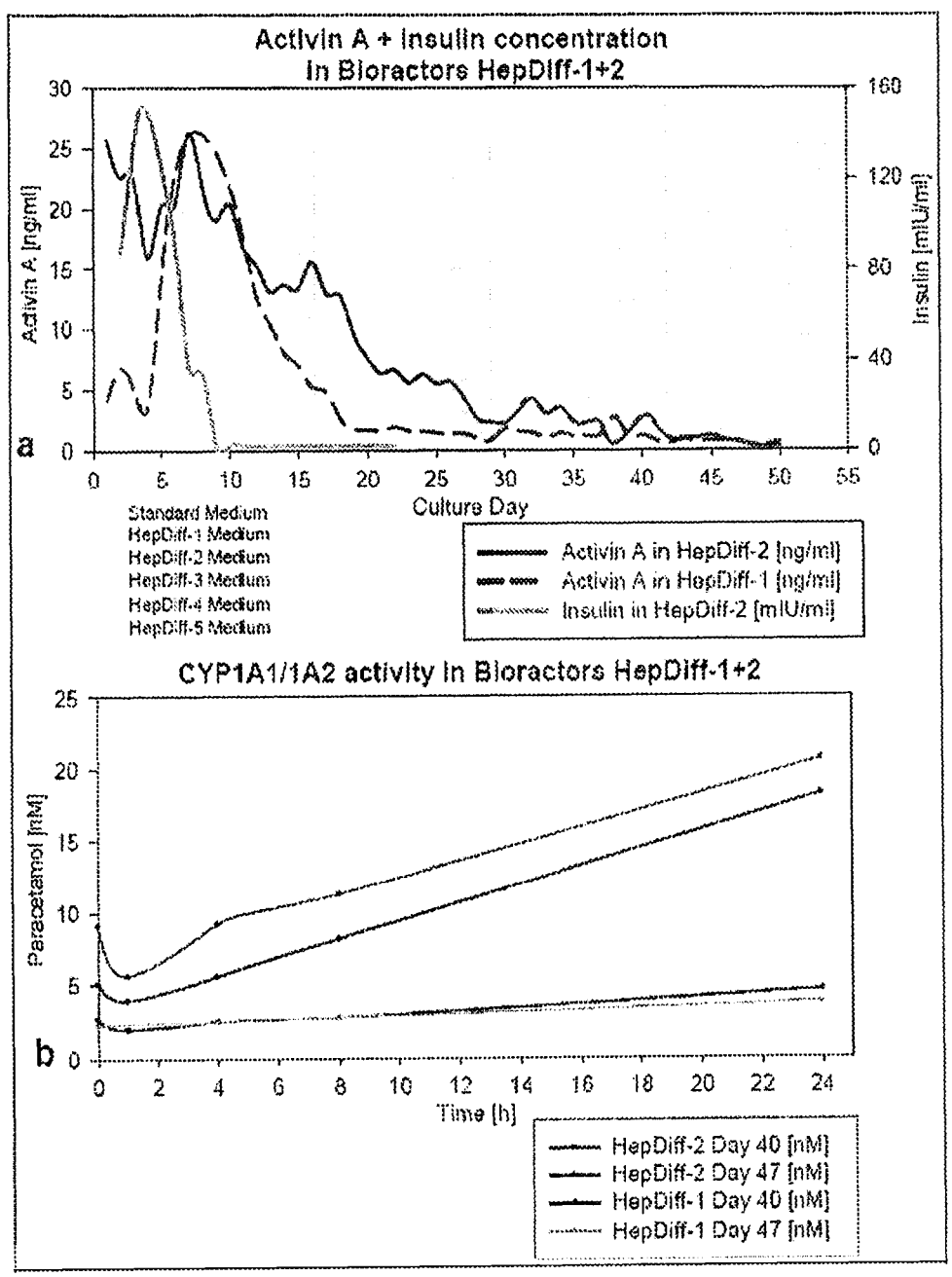
FIGS. 6a-6b. Time course of the activin A and insulin concentrations measured in the medium and cytochrome activity measurement in bioreactors HepDiff-1 and -2. (a) Activin A concentration (pink, dotted and solid, highest curves at day 20) insulin concentration (turquoise, lowest at day 20).
Figure 7:
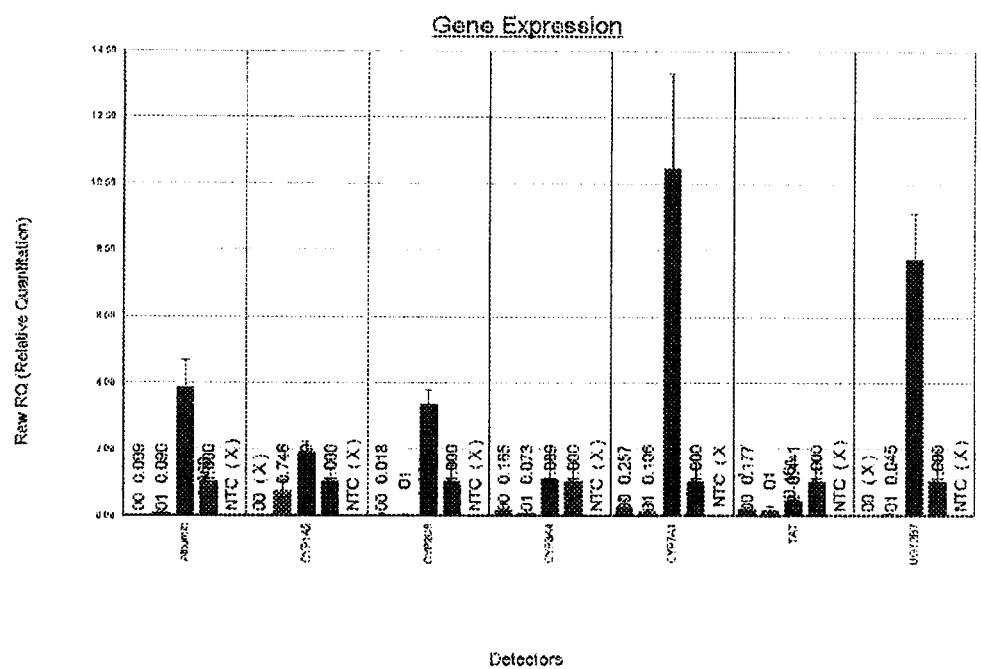
FIG. 7. Histogram of Hepatic marker genes (Albumin, CYP1A2, CYP2C9, CYP3A4, CYP7A1, TAT & UGT2B7) expressed during differentiation and monitored at several time points (Day 0, Day 12, Bioreactor day 26, 2D control day 26)
Figure 8:
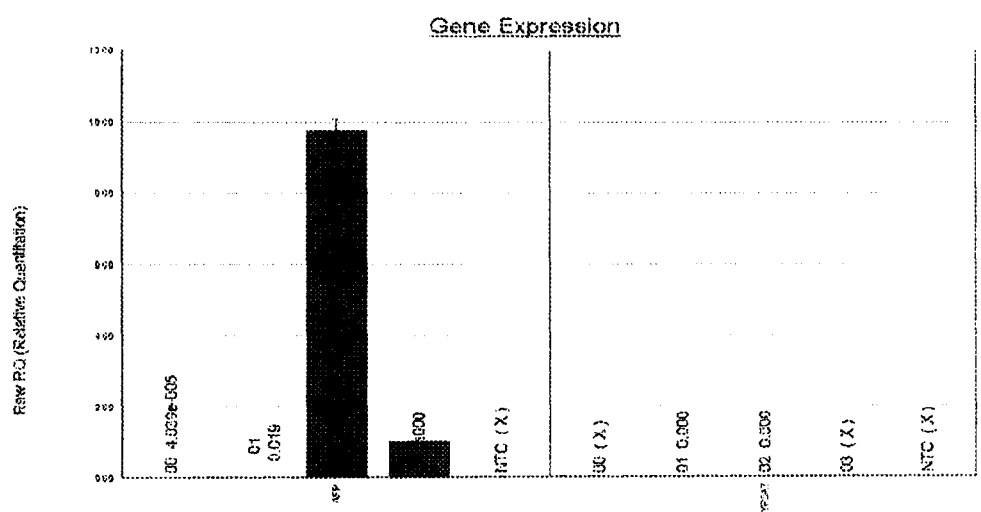
FIG. 8. Histogram of markers for fetal/immature hepatocytes (AFP, CYP3A7) expressed during differentiation and monitored at several time points (Day 0, Day 12, Bioreactor day 26, 2D control day 26)
Figure 9:
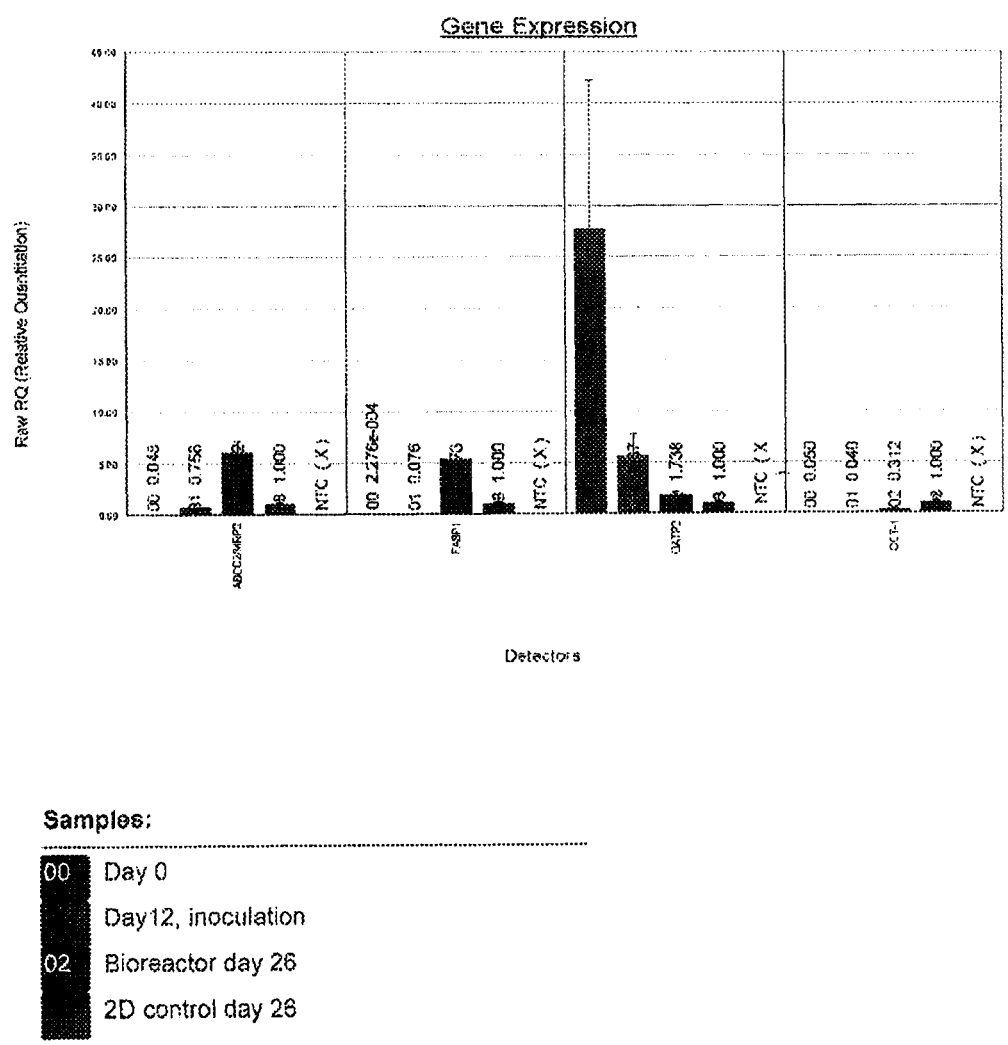
FIG. 9. Histogram of Hepatic transporter genes (ABCC2/MRP2, FABP1, OATP2, OCT-1) expressed during differentiation and monitored at several time points (Day 0, Day 12, Bioreactor day 26, 2D control day 26)
Figure 10:
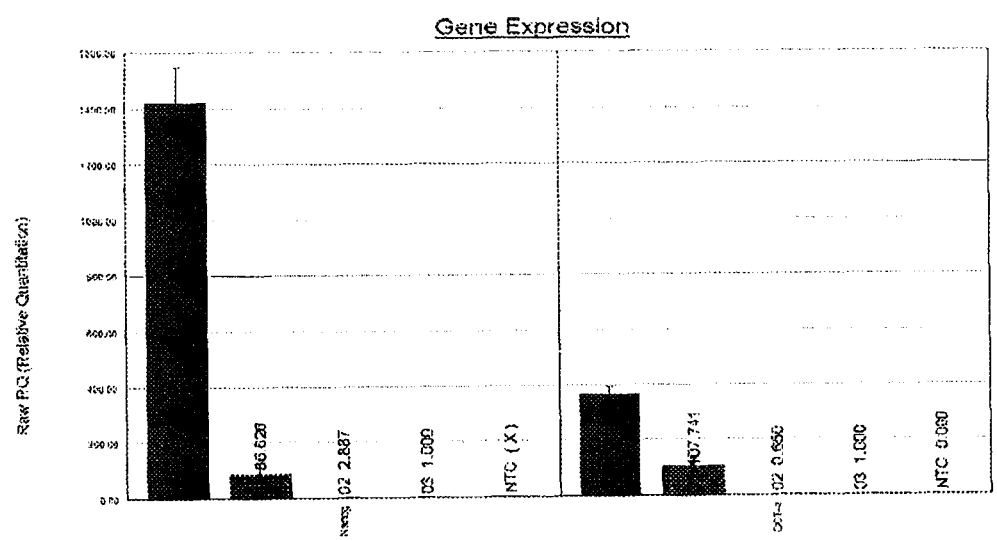
FIG. 10. Histogram of marker genes for undifferentiated cells (Nanog, Oct4) expressed during differentiation and monitored at several time points (Day 0, Day 12, Bioreactor day 26, 2D control day 26)
Figure 11:
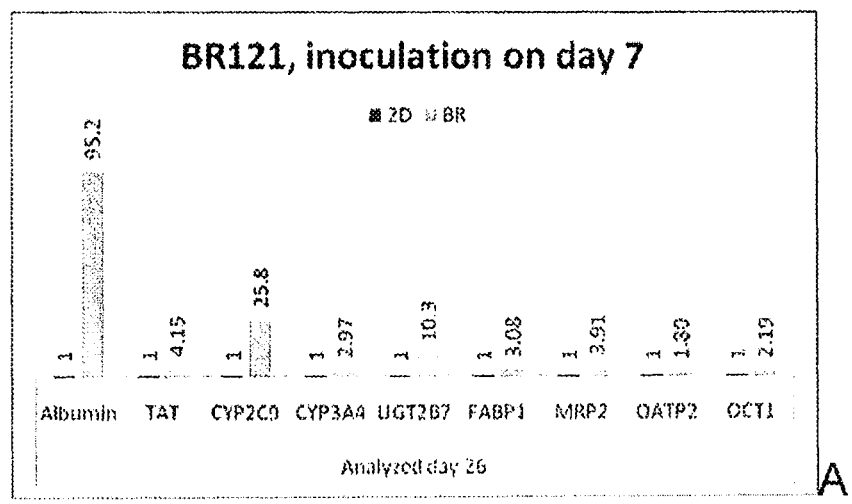
FIGS. 11A-11D. Four histograms (A-D) showing hepatic gene expression profiles of cells inoculated into two different Bioreactors (121 or 168) at different time points. Reference samples with values that equal 1 represent gene expression of cells obtained by 2D culturing.
Figure 11:
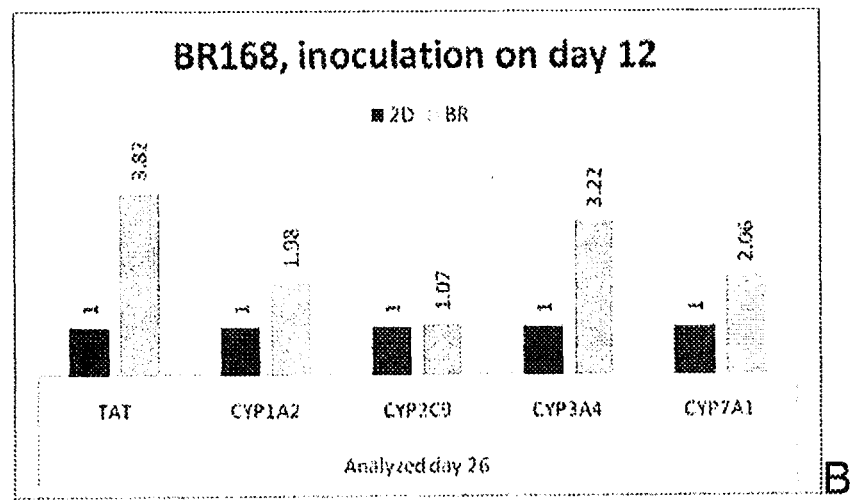
Figure 12:
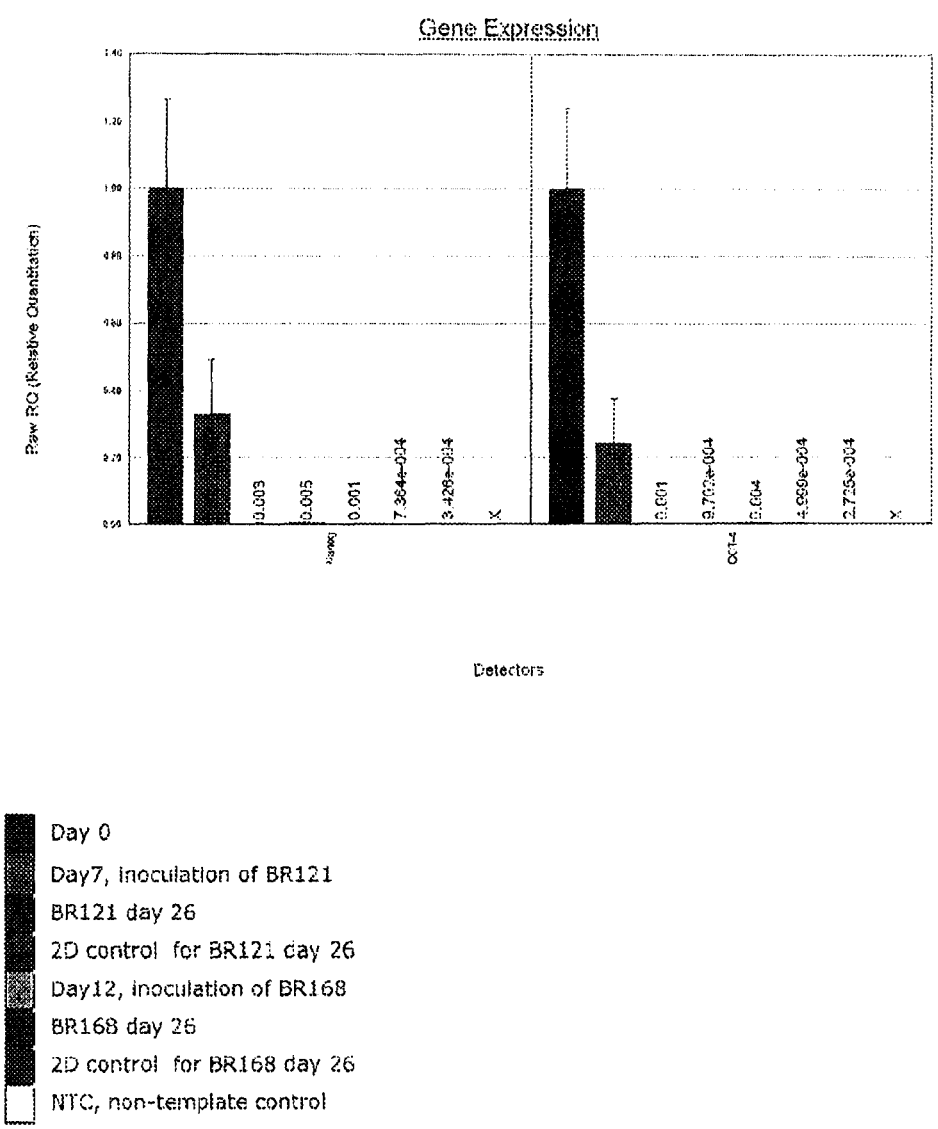
FIG. 12. Histogram showing downregulation of markers of undifferentiated cells (Oct 4 and NANOG) during differentiation and maturation of cells in Bioreactors BR121 and BR168. Reference samples with values that equal 1 represent gene expression of cells obtained by 2D culturing.

Bar, H., S. V. Strelkov, G. Sjoberg, U. Aebi and H. Herrmann (2004). "The biology of desmin filaments: how do mutations affect their structure, assembly, and organisation?" J Struct Biol 148(2): 137-52.

Cai, J., Y. Zhao, Y. Liu, F. Ye, Z. Song, H. Qin, S. Meng, Y. Chen, R. Zhou, X. Song, Y. Guo, M.

Chen, Y. G., Q. Wang, S. L. Lin, C. D. Chang, J. Chuang and S. Y. Ying (2006). "Activin signaling and its role in regulation of cell proliferation, apoptosis, and carcinogenesis." Exp Biol Med (Maywood) 231(5): 534-44.

Conrad, S., M. Renninger, J. Hennenlotter, T. Wiesner, L. Just, M. Bonin, W. Aicher, H. J. Buhring, U. Mattheus, A. Mack, H. J. Wagner, S. Minger, M. Matzkies, M. Reppel, J. Hescheler, K. D. Sievert, A. Stenzl and T. Skutella (2008). "Generation of pluripotent stem cells from adult human testis." Nature 456(7220): 344-9.

Davie, J. R. (2003). "Inhibition of Histone Deacetylase Activity by Butyrate." J. Nutr. 133(7): 2485S-2493-2485S-2493.

Dennis, G., Jr., B. T. Sherman, D. A. Hosack, J. Yang, W. Gao, H. C. Lane and R. A. Lempickii (2003). "DAVID: Database for Annotation, Visualization, and Integrated Discovery." Genome Biol 4(5): P3.

Ding and H. Deng (2007). "Directed differentiation of human embryonic stem cells into functional hepatic cells." Hepatology 45(5): 1229-39.

Eldor and J. A. Thomson (2000). "Clonally derived human embryonic stem cell lines maintain pluripotency and proliferative potential for prolonged periods of culture." Dev Biol 227(2): 271-278.

Evans, M. J. and M. H. Kaufman (1981). "Establishment in culture of pluripotential cells from mouse embryos." Nature 292(5819): 154-6.

Gallicano, G. I., N. Golestaneh, M. Kokkinaki, D. Pant, J. Jiang, D. Destefano, C. Fernandez-Bueno, J. D. Rome, B. R. Haddad and M. Dym (2009). "Pluripotent Stem Cells Derived from Adult Human Testes." Stem Cells Dev.

Gentleman, R. C., V. J. Carey, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. H. Yang and J. Zhang (2004). "Bioconductor: open software development for computational biology and bioinformatics." Genome Biology 5(10): R80—R80.

Gerecht-Nir, S., S. Cohen and J. Itskovitz-Eldor (2004). "Bioreactor cultivation enhances the efficiency of human embryoid body (hEB) formation and differentiation." Biotechnol Bioeng 86(5): 493-502.

Gerlach, J. C., J. Encke, O. Hole, C. M_ller, C. J. Ryan and P. Neuhaus (1994). "Bioreactor for a larger scale hepatocyte in vitro perfusion." Transplantation 58(9): 984-8.

Gerlach, J. C., K. Mutig, I. M. Sauer, P. Schrade, E. Efimova, T. Mieder, G. Naumann, A.

Hay, D. C., D. Zhao, J. Fletcher, Z. A. Hewitt, D. McLean, A. Urruticoechea-Uriguen, J. R. Black, C. Elcombe, J. A. Ross, R. Wolf and W. Cui (2008). "Efficient differentiation of hepatocytes from human embryonic stem cells exhibiting markers recapitulating liver development in vivo." Stem Cells 26(4): 894-902.

Hay, D. C., D. Zhao, A. Ross, R. Mandalam, J. Lebkowski and W. Cui (2007). "Direct differentiation of human embryonic stem cells to hepatocyte-like cells exhibiting functional activities." Cloning Stem Cells 9(1): 51-62.

Heng, B. C., H. Yu, Y. Yin, S. G. Lim and T. Cao (2005). "Factors influencing stem cell differentiation into the hepatic lineage in vitro." J Gastroenterol Hepatol 20(7): 975-87.

Hines, R. N. and D. G. McCarver (2002). "The ontogeny of human drug-metabolizing enzymes: phase I oxidative enzymes." J Pharmacol Exp Ther 300(2): 355-60.

Itskovitz-Eldor, J., M. Schuldiner, D. Karsenti, A. Eden, O. Yanuka, M. Amit, H. Soreq and N. Benvenisty (2000). "Differentiation of human embryonic stem cells into embryoid bodies compromising the three embryonic germ layers." Molecular Medicine 6(2): 88?95-88?95.

Jensen, J., J. Hyllner and P. Bjorquist (2009). "Human embryonic stem cell technologies and drug discovery." J Cell Physiol 219(3): 513-9.

Kossack, N., J. Meneses, S. Shefi, H. N. Nguyen, S. Chavez, C. Nicholas, J. Gromoll, P. J. Turek and R. A. Reijo-Pera (2008). "Isolation and Characterization of Pluripotent Human Spermatogonial Stem Cell-Derived Cells." Stem Cells.

Kubo, A., K. Shinozaki, J. M. Shannon, V. Kouskoff, M. Kennedy, S. Woo, H. J. Fehling and G. Keller (2004). "Development of definitive endoderm from embryonic stem cells in culture." Development 131(7): 1651-1662.

Kuhn, K., S. C. Baker, E. Chudin, M. H. Lieu, S. Oeser, H. Bennett, P. Rigault, D. Barker, T. K. McDaniel and M. S. Chee (2004). "A novel, high-performance random array platform for quantitative gene expression profiling." Genome Res 14(11): 2347-56.

Lavon, N., O. Yanuka and N. Benvenisty (2004). "Differentiation and isolation of hepatic-like cells from human embryonic stem cells." Differentiation 72(5): 230-8.

Levenberg, S., N. F. Huang, E. Lavik, A. B. Rogers, J. ltskovitz-Eldor and R. Langer (2003). "Differentiation of human embryonic stem cells on three-dimensional polymer scaffolds." Proceedings of the National Academy of Sciences of the United States of America 100(22): 12741-6.

Li, Y., D. A. Kniss, L. C. Lasky and S.-T. Yang (2003). "Culturing and differentiation of murine embryonic stem cells in a three-dimensional fibrous matrix." Cytotechnology 41(1): 23-35.

Li, Y., S. Powell, E. Brunette, J. Lebkowski and R. Mandalam (2005). "Expansion of human embryonic stem cells in defined serum-free medium devoid of animal-derived products." Biotechnol. Bioeng. 91(6): 688-698.

Ludwig, T. E., M. E. Levenstein, J. M. Jones, W. T. Berggren, E. R. Mitchen, J. L. Frane, L. J. Crandall, C. A. Daigh, K. R. Conard, M. S. Piekarczyk, R. A. Llanas and J. A. Thomson (2006). "Derivation of human embryonic stem cells in defined conditions." Nat. Biotechnol. 24(2): 185-187.

Pera, M. F. and A. O. Trounson (2004). "Human embryonic stem cells: prospects for development." Development 131 (22): 5515-25.

Przyborski, S. A. (2005). "Differentiation of human embryonic stem cells after transplantation in immune-deficient mice." Stem Cells 23(9): 1242-50.

Rambhatla, L., C. P. Chiu, P. Kundu, Y. Peng and M. K. Carpenter (2003). "Generation of hepatocyte-like cells from human embryonic stem cells." Cell Transplant 12(1): 1-11.

Rao, M. (2004). "Conserved and divergent paths that regulate self-renewal in mouse and human embryonic stem cells." Dev Biol 275(2): 269-86.

Saeed, A. I., V. Sharov, J. White, J. Li, W. Liang, N. Bhagabati, J. Braisted, M. Klapa, T. Currier, M. Thiagarajan, A. Sturn, M. Snuffin, A. Rezantsev, D. Popov, A. Ryltsov, E. Kostukovich, I. Borisovsky, Z. Liu, A. Vinsavich, V. Trush and J. Quackenbush (2003). "TM4: a free, open-source system for microarray data management and analysis." BioTechniques 34(2): 374-8.

Sartipy, P., P. Bjorquist, R. Strehl and J. Hyllner (2007). "The application of human embryonic stem cell technologies to drug discovery." Drug Discov Today 12(17-18): 688-99.

Sauer, I. M., K. Zeilinger, G. Pless, D. Kardassis, T. Theruvath, A. Pascher, M. Goetz, P. Neuhaus and J. C. Gerlach (2003). "Extracorporeal liver support based on primary human liver cells and albumin dialysis—treatment of a patient with primary graft nonfunction." J Hepatol 39(4): 649-53.

Schuldiner, M., O. Yanuka, J. Itskovitz-Eldor, D. A. Melton and N. Benvenisty (2000). "Effects of eight growth factors on the differentiation of cells derived from human embryonic stem cells." Proc. Natl. Acad. Sci. USA 97(21): 11307-11312.

Shih, C. C., Y. Weng, A. Mamelak, T. LeBon, M. C. Hu and S. J. Forman (2001). "Identification of a candidate human neurohematopoietic stem-cell population." Blood 98(8): 2412-22.

Snykers, S., J. De Kock, V. Rogiers and T. Vanhaecke (2008). "In vitro differentiation of embryonic and adult stem cells into hepatocytes: state of the art." Stem Cells: stemcells. 2008-0963-stemcells. 2008-0963.

Soto-Gutierrez, A., N. Navarro-Alvarez, J. D. Rivas-Carrillo, Y. Chen, T. Yamatsuji, N. Tanaka and N. Kobayashi (2006). "Differentiation of human embryonic stem cells to hepatocytes using deleted variant of HGF and poly-amino-urethane-coated nonwoven polytetrafluoroethylene fabric." Cell Transplant 15(4): 335-41.

Takahashi, K., K. Tanabe, M. Ohnuki, M. Narita, T. Ichisaka, K. Tomoda and S. Yamanaka (2007). "Induction of pluripotent stem cells from adult human fibroblasts by defined factors." Cell 131(5): 861-72.

Takahashi, K. and S. Yamanaka (2006). "Induction of pluripotent stem cells from mouse embryonic and adult fibroblast cultures by defined factors." Cell 126(4): 663-76.

Thomson, J. A., J. Kalishman, T. G. Golos, M. Durning, C. P. Harris, R. A. Becker and J. P. Hearn (1995). "Isolation of a primate embryonic stem cell line." Proceedings of the National Academy of Sciences of the United States of America 92(17): 7844-8.

Wang, L., T. C. Schulz, E. S. Sherrer, D. S. Dauphin, S. Shin, A. M. Nelson, C. B. Ware, M. Zhan, C. Z. Song, X. Chen, S, N. Brimble, A. McLean, M. J. Galeano, E. W. Uhl, K. A. D'Amour, J. D. Chesnut, M. S. Rao, C. A. Blau and A. J. Robins (2007). "Self-renewal of human embryonic stem cells requires insulin-like growth factor-1 receptor and ERBB2 receptor signaling." Blood 110(12): 4111-9.

Xie, C. Q., G. Lin, D. Yuan, J. Wang, T. C. Liu and G. X. Lu (2005). "Proliferative feeder cells support prolonged expansion of human embryonic stem cells." Cell Biol Int 29(8): 623-8.

Xie, J., S. M. Willerth, X. Li, M. R. Macewan, A. Rader, S. E. Sakiyama-Elbert and Y. Xia (2009). "The differentiation of embryonic stem cells seeded on electrospun nanofibers into neural lineages." Biomaterials 30(3): 354-362.

The invention claimed is:

1. A method for differentiation of human pluripotent stem cells into cells expressing mature hepatocyte markers comprising:

i) culturing human pluripotent stem (hPS) cells in a 2D feeder-free culture system in a low serum culture medium comprising Activin A to produce cells differentiating towards definitive endoderm (DE);

ii) seeding the cells of step i) in a bioreactor;

iii) perfusing the bioreactor with one or more culture media selected from a medium comprising low serum, bFGF and Activin A; a medium comprising serum, bFGF and Activin A; or a medium comprising serum, aFGF, bFGF, BMP2 and BMP4 to induce differentiation of DE into cells expressing AFP at about day 17; and iv) perfusing the bioreactors containing the AFP expressing cells of step ii) with a culture medium comprising bFGF, HGF, Oncostatin M, and Dexamethasone or in a culture medium comprising HGF, Oncostatin M, Dexamethasone, and DMSO, wherein resulting cells express AFP, albumin and urea; wherein the perfused cells of step (ii) differentiate into cells that express the mature hepatic markers Albumin, CYP3A4, UGT2B7, OATP-2, ADH1A, UGTIA6, CYP2C9, CYP2C19, and CYP2D6.

2. The method according to claim 1, wherein the cells expressing mature hepatocyte markers form a 3D tissue structure.

3. The method according to claim 1 or 2, wherein the hPS cells are human embryonic stem cells.

4. The method according to claim 1 or 2, wherein the hPS cells are induced pluripotent stem (iPS) cells.

5. The method according to claim 1, wherein the bioreactor is a hollow fiber capillary bioreactor.

6. The method according to claim 1, wherein the bioreactor is provided with membrane compartments.

7. The method according to claim 6, wherein the membrane compartments comprise two or more capillary systems and one or more hollow fiber membrane.

8. The method according to any one of claims 5 to 7, wherein the bioreactor comprises a capillary system for perfusion of culture medium through the capillary system and a capillary system for gas exchange.

9. The method according to claim 8, wherein perfusion of growth medium takes place through the capillary system and gas exchange takes place via a hollow fiber membrane system.

10. The method according to claim 9, wherein the capillary system and one or more hollow fiber membranes are configured to form independent interwoven fiber capillary membrane systems integrated into a housing.

11. The method according to claim 1, wherein the bioreactor is inoculated with inactivated fibroblast feeder cells prior to step ii).

12. The method according to claim 11, wherein the feeder cells are human foreskin fibroblasts (hFF) or mouse embryonic feeder (MEF) cells.

13. The method according to claim 1, wherein the bioreactor is co-inoculated with human blastocyst-derived stem (hBS) cells and inactivated fibroblast feeder cells or definitive endoderm cells and inactivated fibroblast feeder cells.

14. The method according to claim 1, wherein the culture media comprises a cell survival factor.

15. The method according to claim 1, wherein the culture media comprises an inhibitor of ROCK Rho kinase.

* * * * *